(12) United States Patent
Lin et al.

(10) Patent No.: US 10,497,120 B2
(45) Date of Patent: Dec. 3, 2019

(54) METHOD AND APPARATUS OF FIBER TRACKING, AND NON-TRANSITORY COMPUTER-READABLE MEDIUM THEREOF

(71) Applicants: Ching-Po Lin, Taipei (TW); Shin-Tai Chong, Taipei (TW); Chun-Yi Lo, Taipei (TW); Chu-Chung Huang, Taipei (TW)

(72) Inventors: Ching-Po Lin, Taipei (TW); Shin-Tai Chong, Taipei (TW); Chun-Yi Lo, Taipei (TW); Chu-Chung Huang, Taipei (TW)

(73) Assignee: NATIONAL YING-MING UNIVERSITY, Taipei (TW)

( * ) Notice: Subject to any disclaimer, the term of this patent is extended or adjusted under 35 U.S.C. 154(b) by 95 days.

(21) Appl. No.: 15/953,456

(22) Filed: Apr. 15, 2018

(65) Prior Publication Data

US 2019/0318480 A1   Oct. 17, 2019

(51) Int. Cl.
*G06K 9/00* (2006.01)
*G06T 7/00* (2017.01)
(Continued)

(52) U.S. Cl.
CPC ............ *G06T 7/0016* (2013.01); *A61B 6/032* (2013.01); *A61B 6/501* (2013.01); *A61B 6/506* (2013.01);
(Continued)

(58) Field of Classification Search
CPC ......... G06T 7/0016; G06T 2207/10081; G06T 2207/10088; G06T 2207/30016; A61B 6/032; A61B 6/501; A61B 6/506
See application file for complete search history.

(56) References Cited

U.S. PATENT DOCUMENTS 10,013,770 B2 * 7/2018 Seiler .................... G06T 7/13
2013/0315448 A1 * 11/2013 Fletcher ................. G06T 7/33
382/107

(Continued)

OTHER PUBLICATIONS

Lin, Ching-Po, et al. "Validation of diffusion spectrum magnetic resonance imaging with manganese-enhanced rat optic tracts and ex vivo phantoms." Neuroimage 19.3 (2003): 482-495.*

(Continued)

*Primary Examiner* — Shefali D Goradia
(74) *Attorney, Agent, or Firm* — Chih Feng Yeh; Huntington IP Consulting Co., Ltd.

(57) ABSTRACT

The present disclosure illustrates a method and an apparatus of fiber tracking, and non-transitory computer-readable medium thereof. In an embodiment, a fiber tracking process is performed on a diffusion magnetic resonance image of a subject's brain based on validated and better tracking parameters, so as to obtain first tracking images, nerve fibers between two first regions of interest in each of the first tracking images are extracted, a nerve fasciculus skeleton is established based on an overlapping process performed on the plurality of nerve fibers extracted from the first tracking images, and the nerve fibers more similar to the structure of the nerve fasciculus skeleton are selected to obtain a specific fasciculus of the subject. Thus, the technical solution of the present disclosure can be used to improve the sensitivity of fiber tracking and be useful for improvement of preoperative assessment and surgical navigation.

9 Claims, 16 Drawing Sheets

(51) Int. Cl.
*A61B 6/03* (2006.01)
*A61B 6/00* (2006.01)
(52) U.S. Cl.
CPC ............... *G06T 2207/10081* (2013.01); *G06T 2207/10088* (2013.01); *G06T 2207/30016* (2013.01)

(56) References Cited

U.S. PATENT DOCUMENTS

2017/0184696 A1* 6/2017 Zuccolotto ............. A61B 5/055
2018/0005380 A1* 1/2018 Seiler ...................... G06T 7/181

OTHER PUBLICATIONS

Watts, Richard, et al. "Fiber tracking using magnetic resonance diffusion tensor imaging and its applications to human brain development." Mental retardation and developmental disabilities research reviews 9.3 (2003): 168-177.*

* cited by examiner

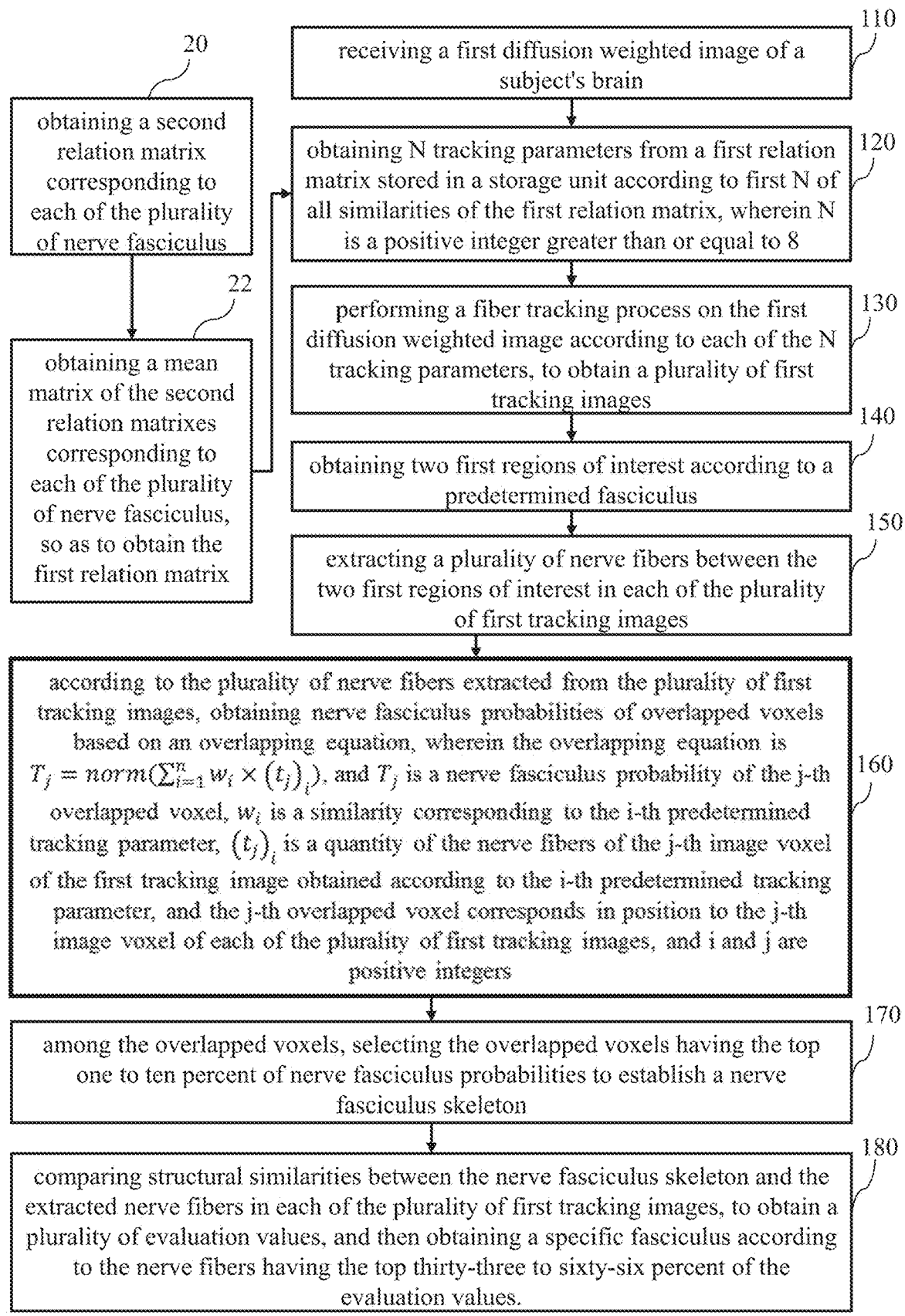
[FIG. 1]

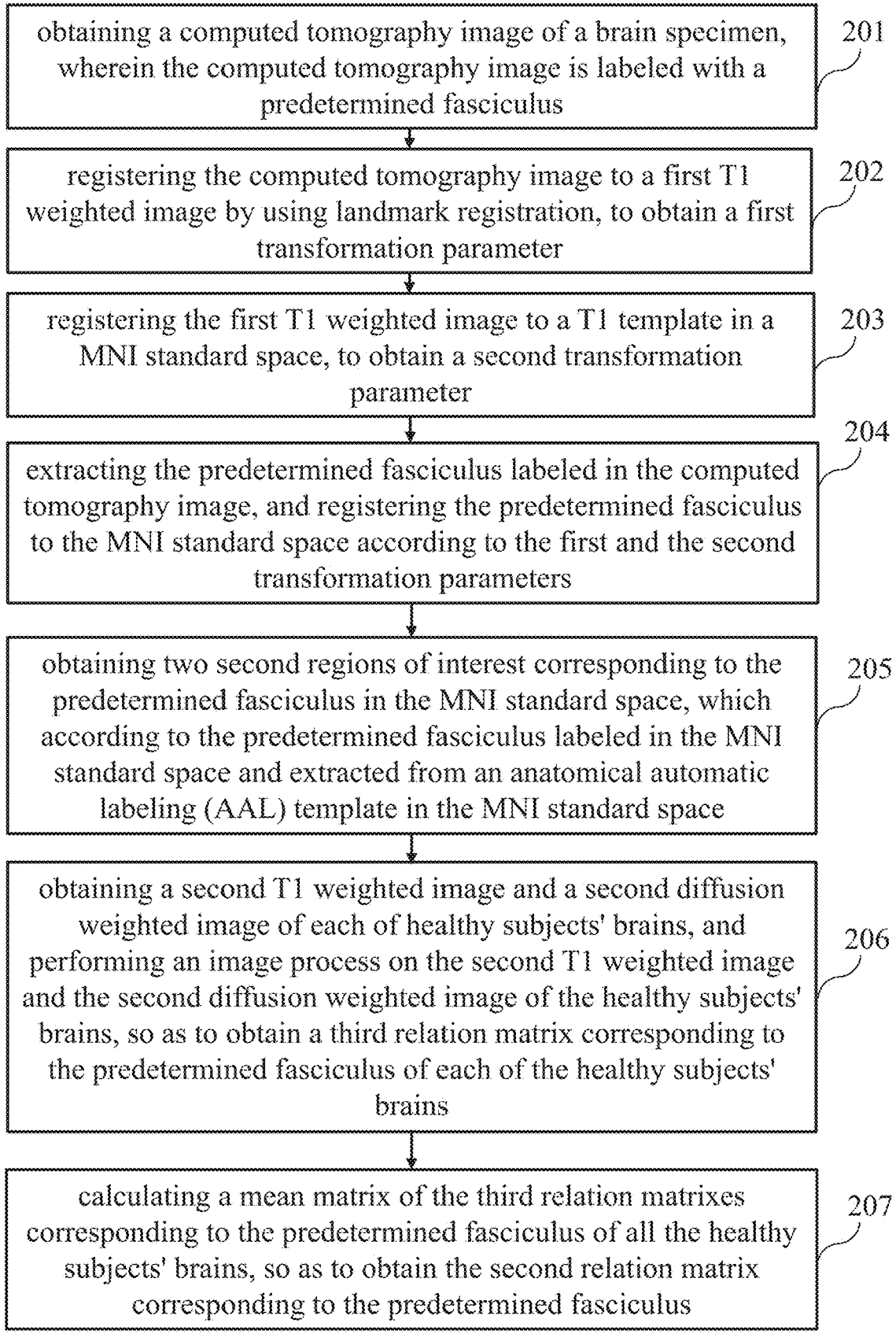
[FIG. 2]

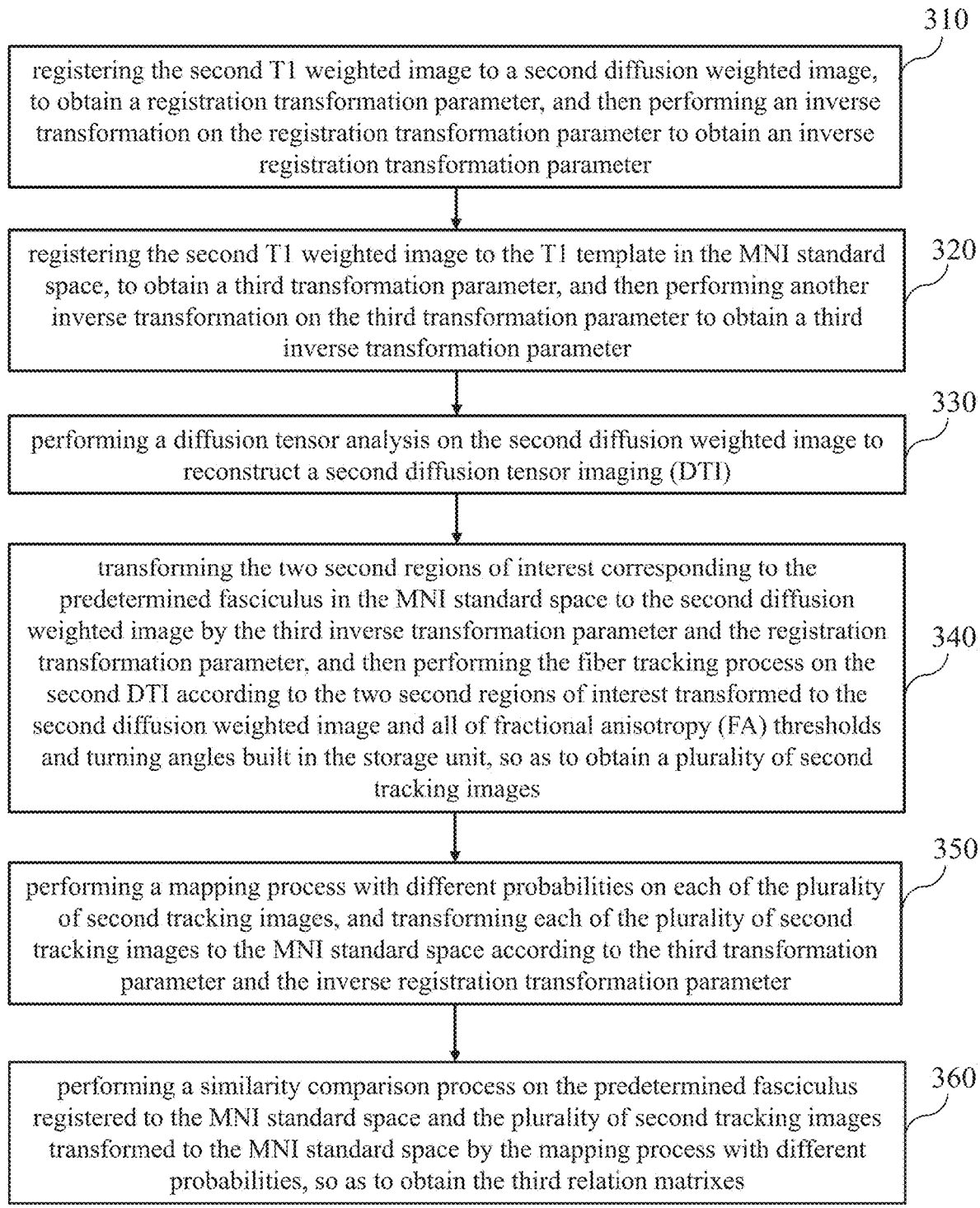
[ FIG. 3 ]

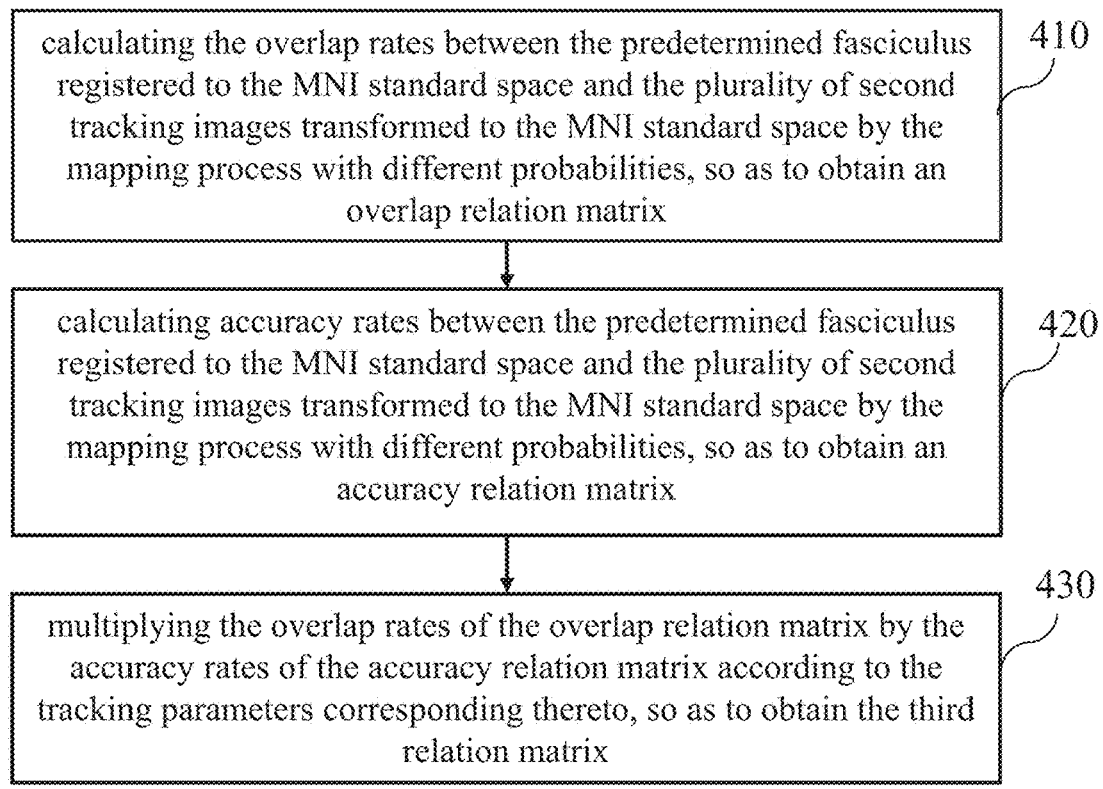
[ FIG. 4 ]
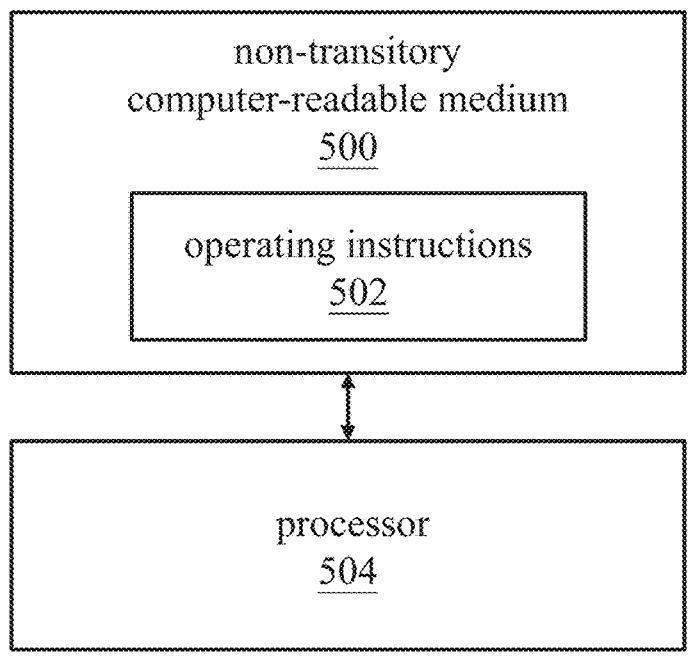
[ FIG. 5 ]

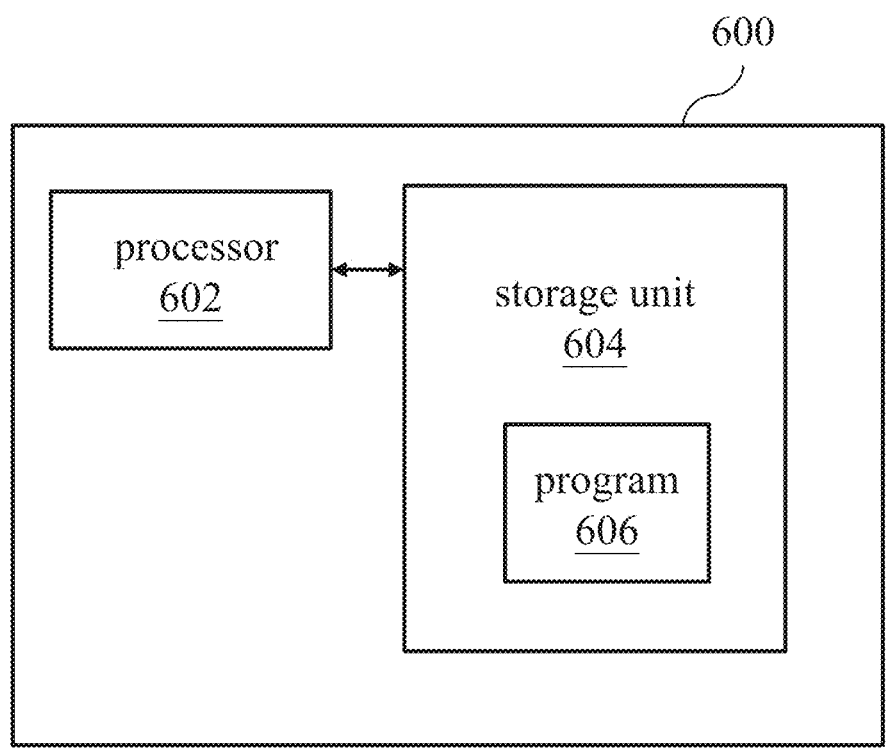
[ FIG. 6 ]

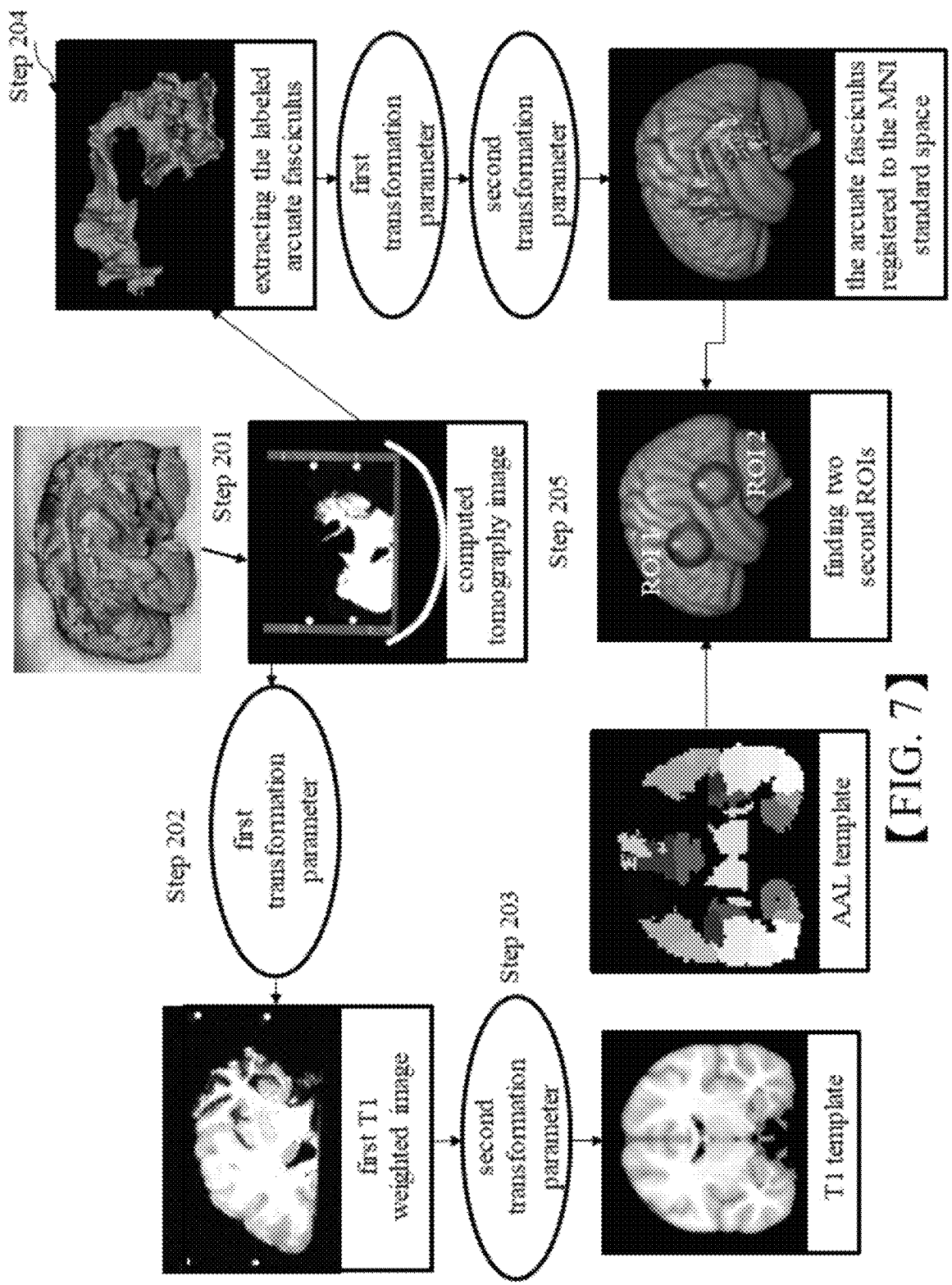
(FIG. 7)

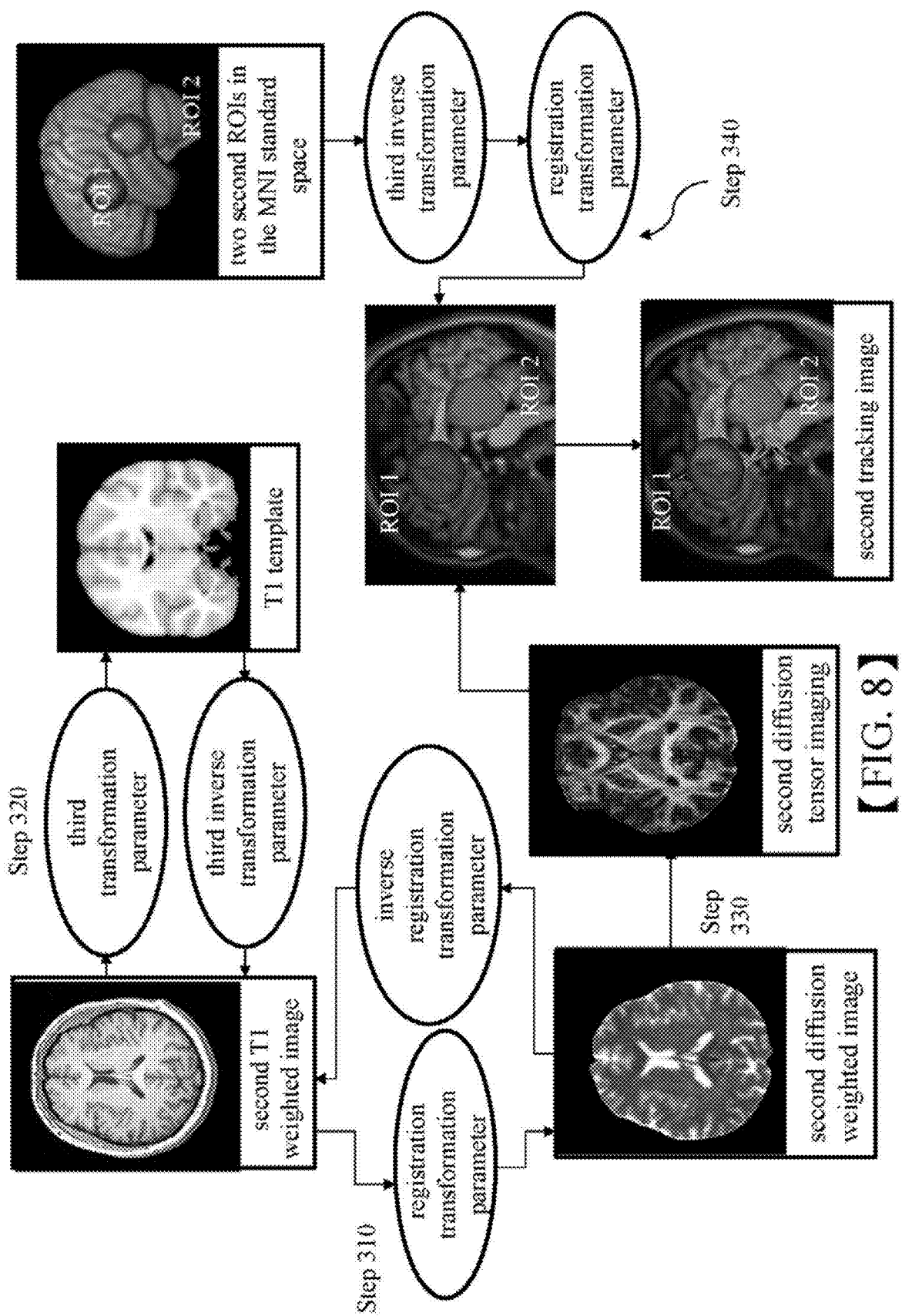
[FIG. 8]

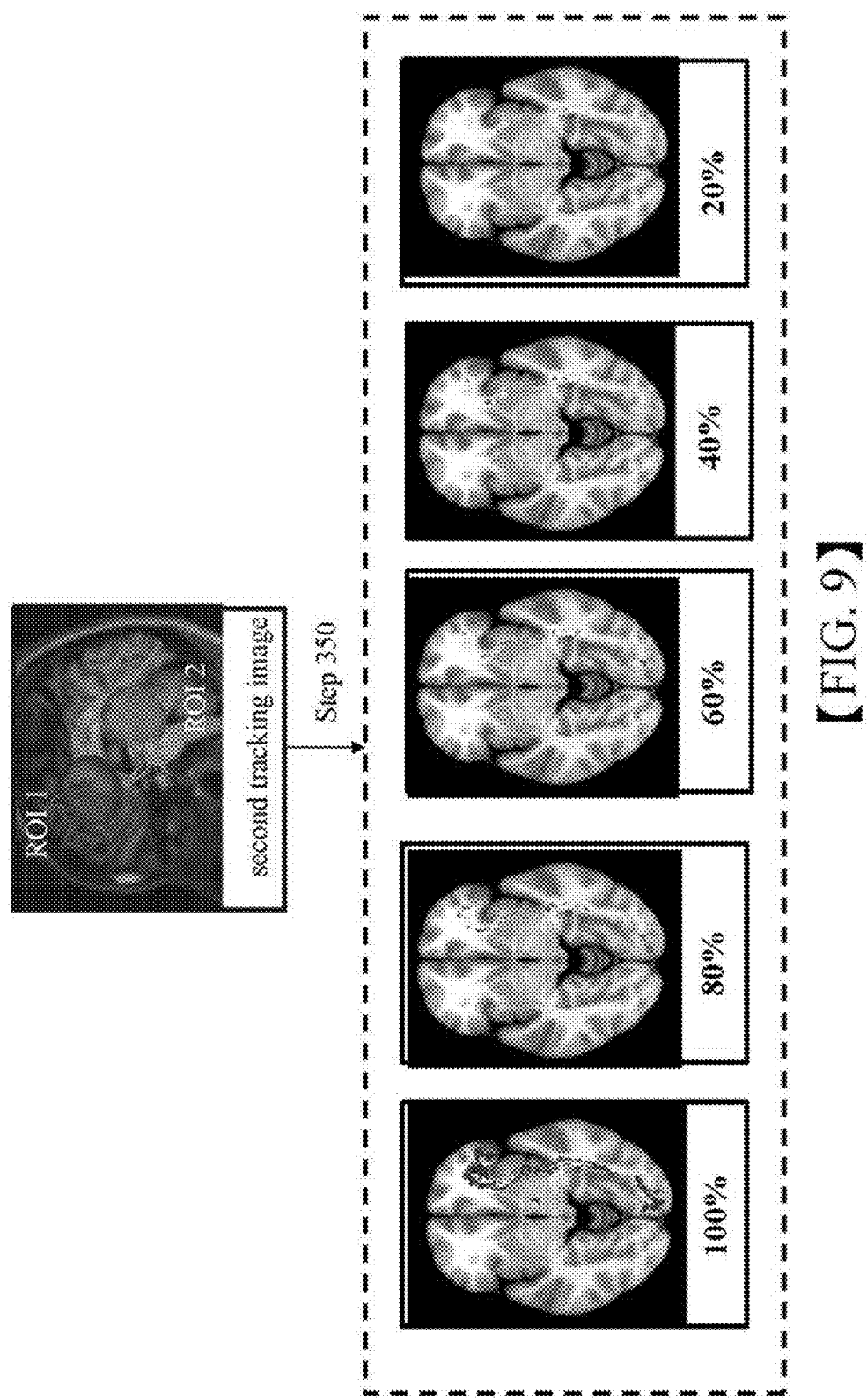
[FIG. 9]

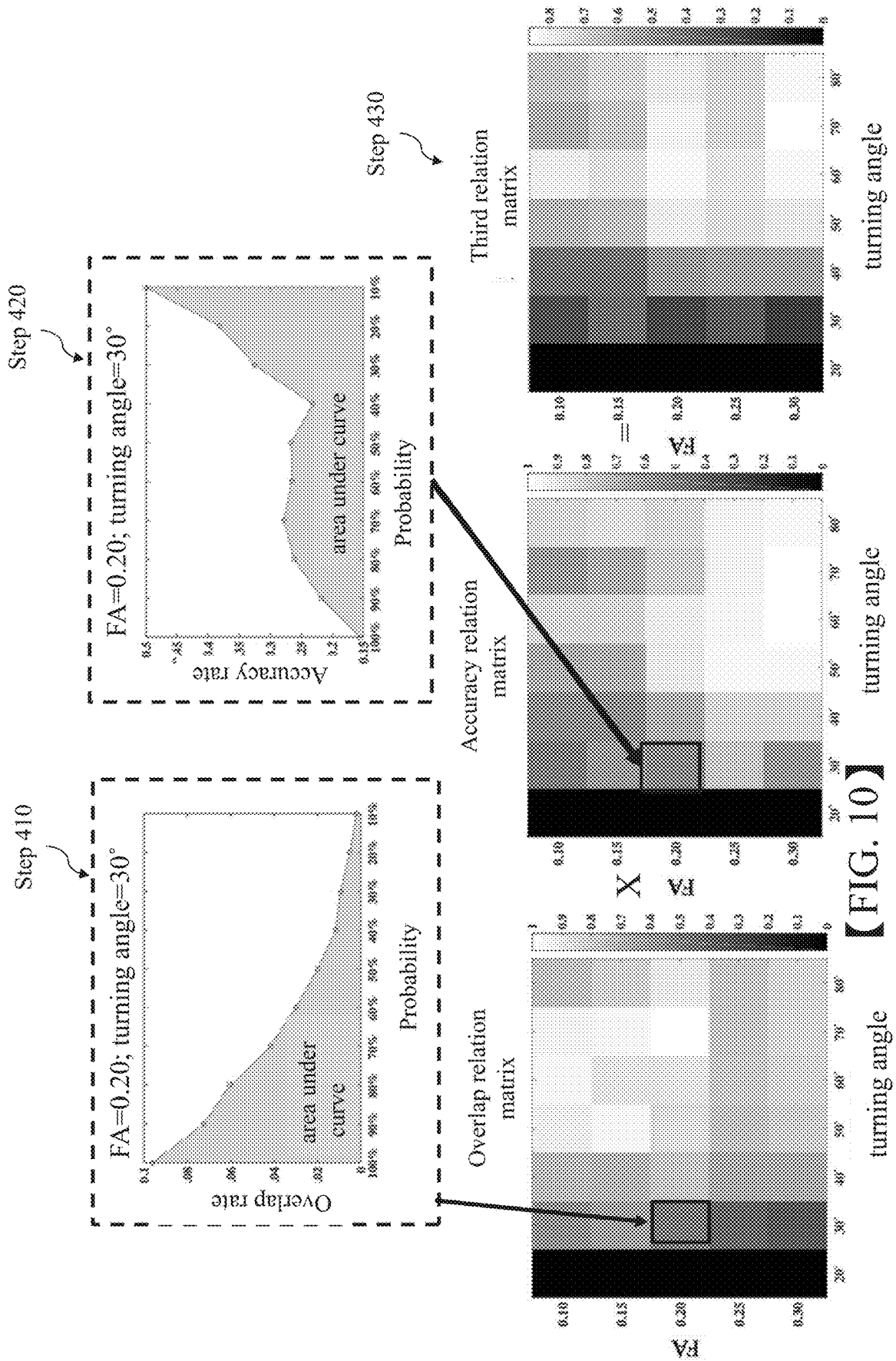
[FIG. 10]

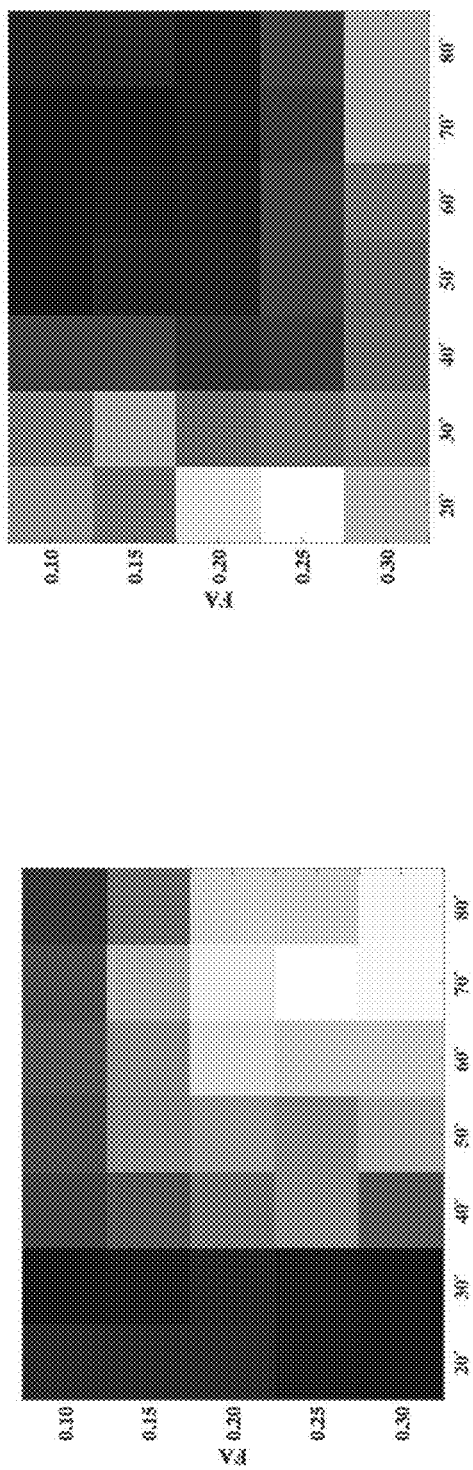
[FIG. 11A] [FIG. 11B]
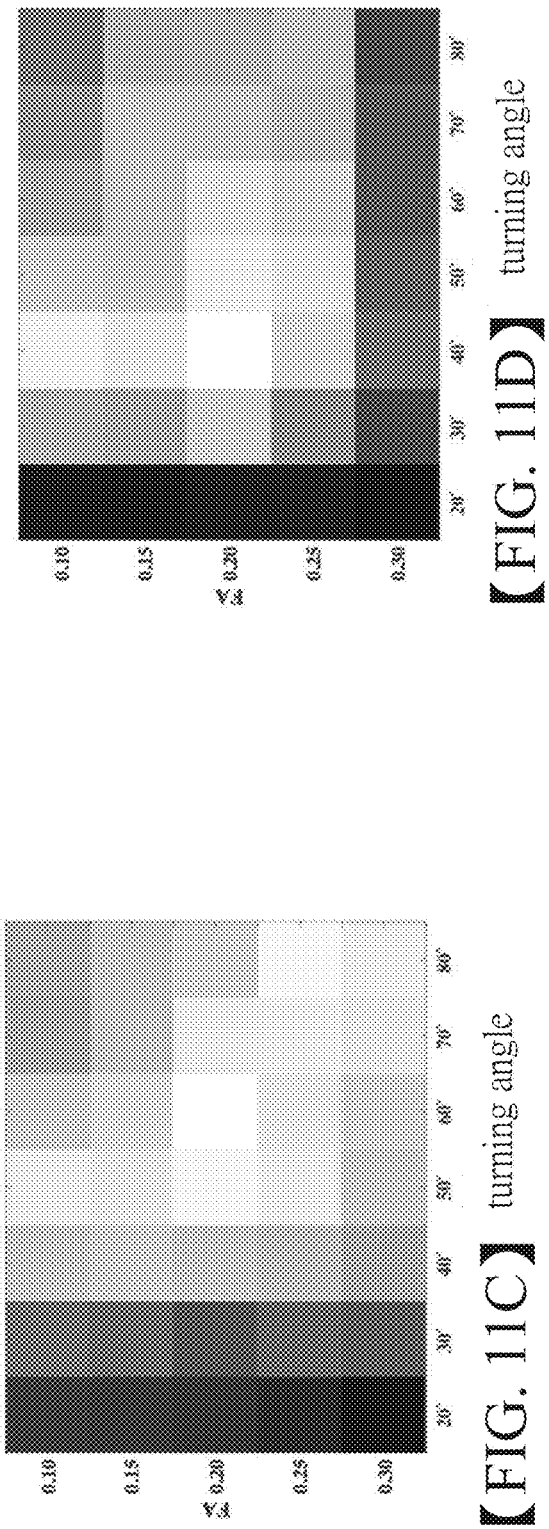
[FIG. 11C] [FIG. 11D]

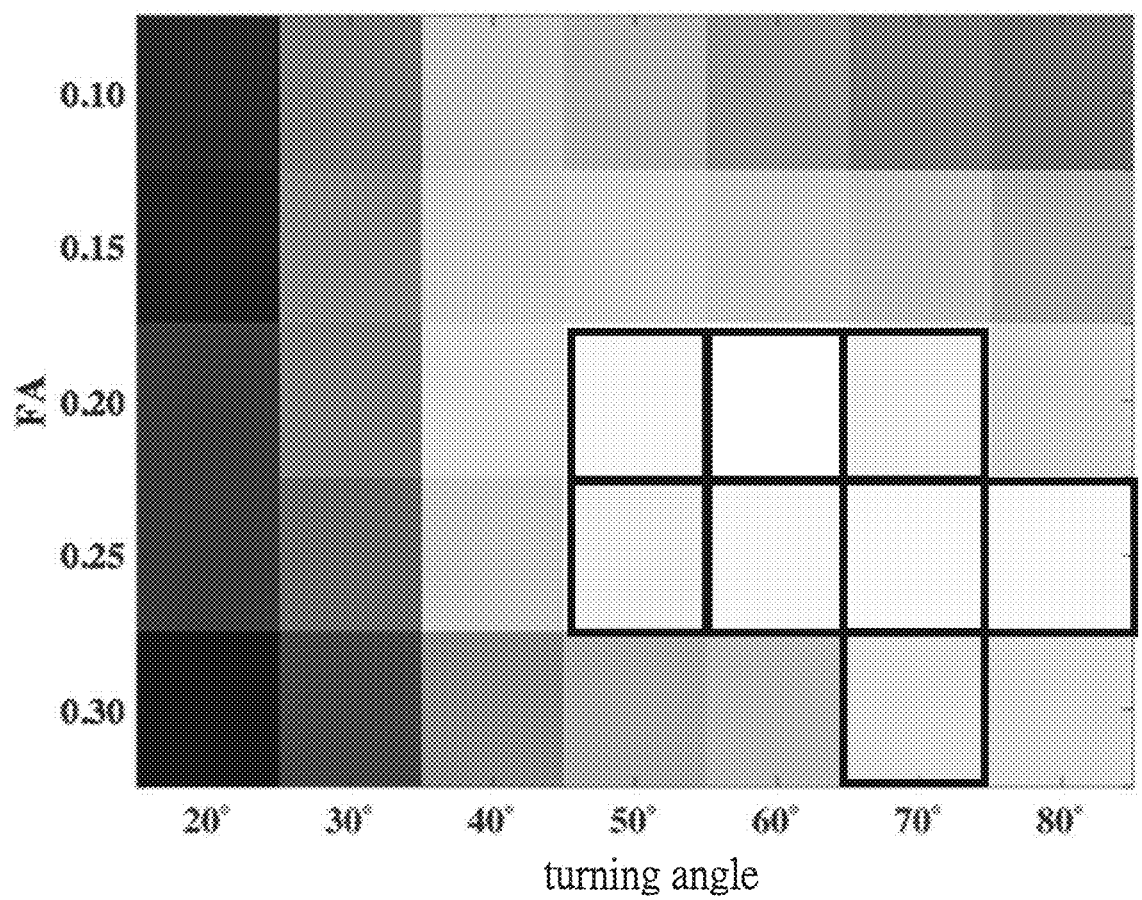
[FIG. 12]

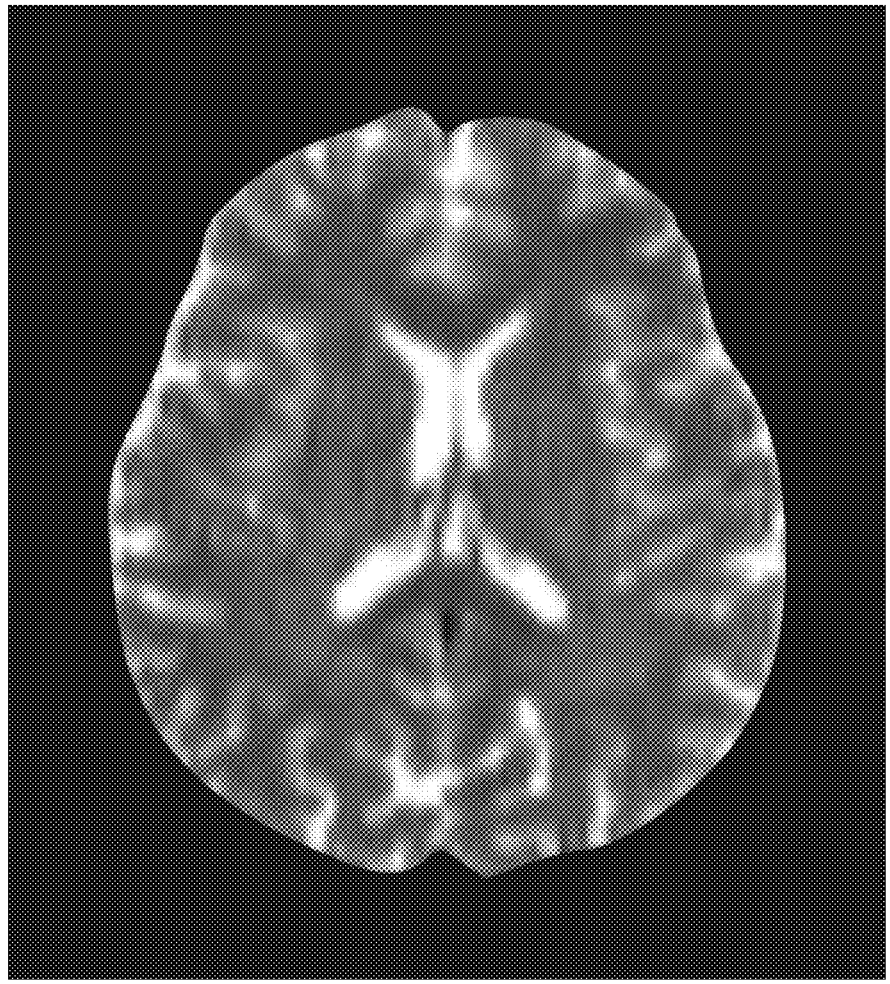
[FIG. 13]

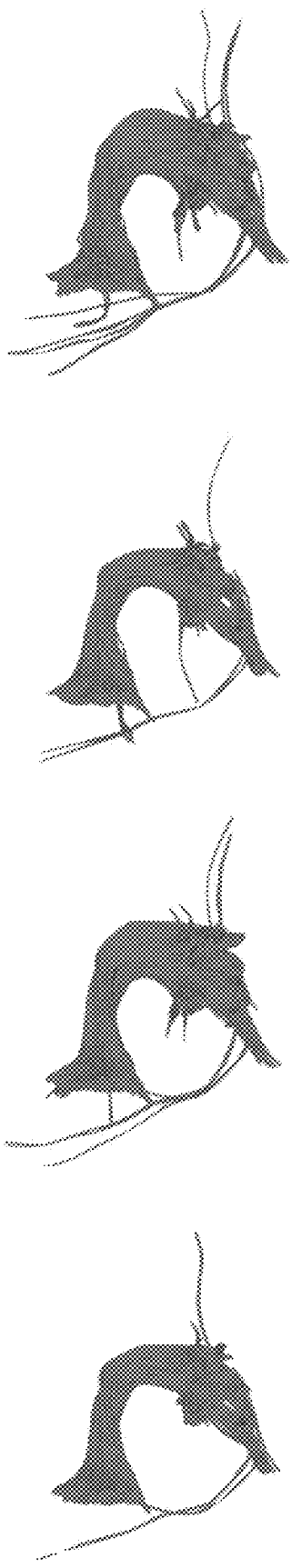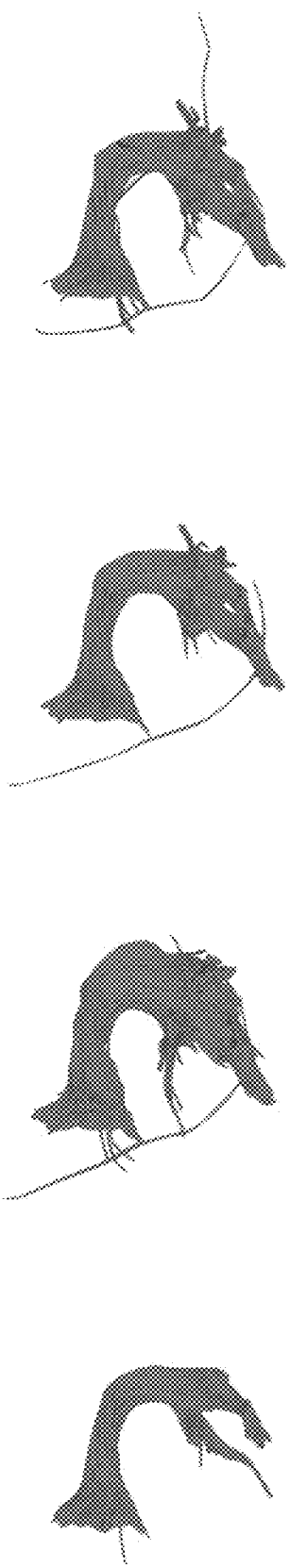
[FIG. 14]

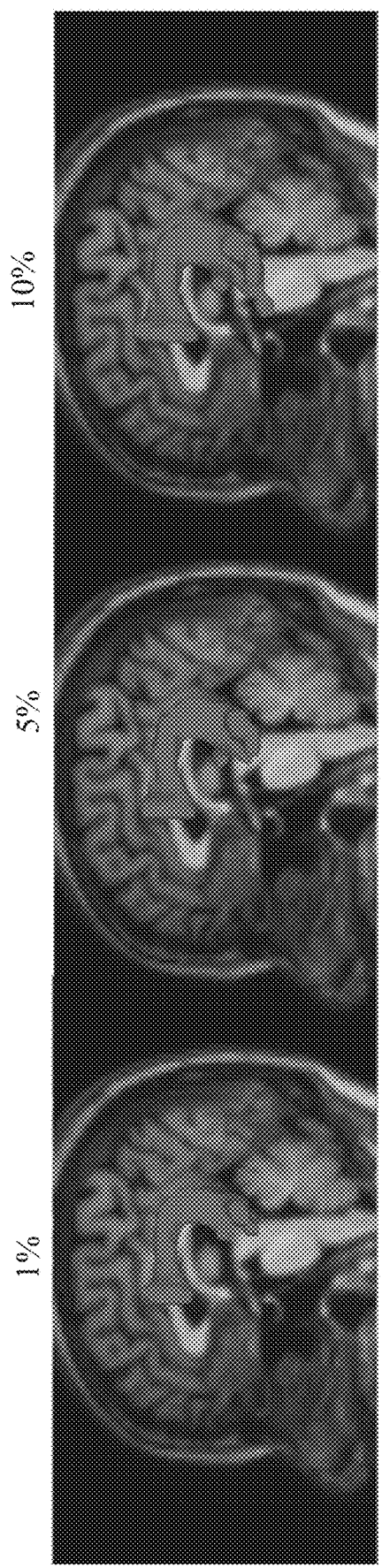
(FIG. 15)

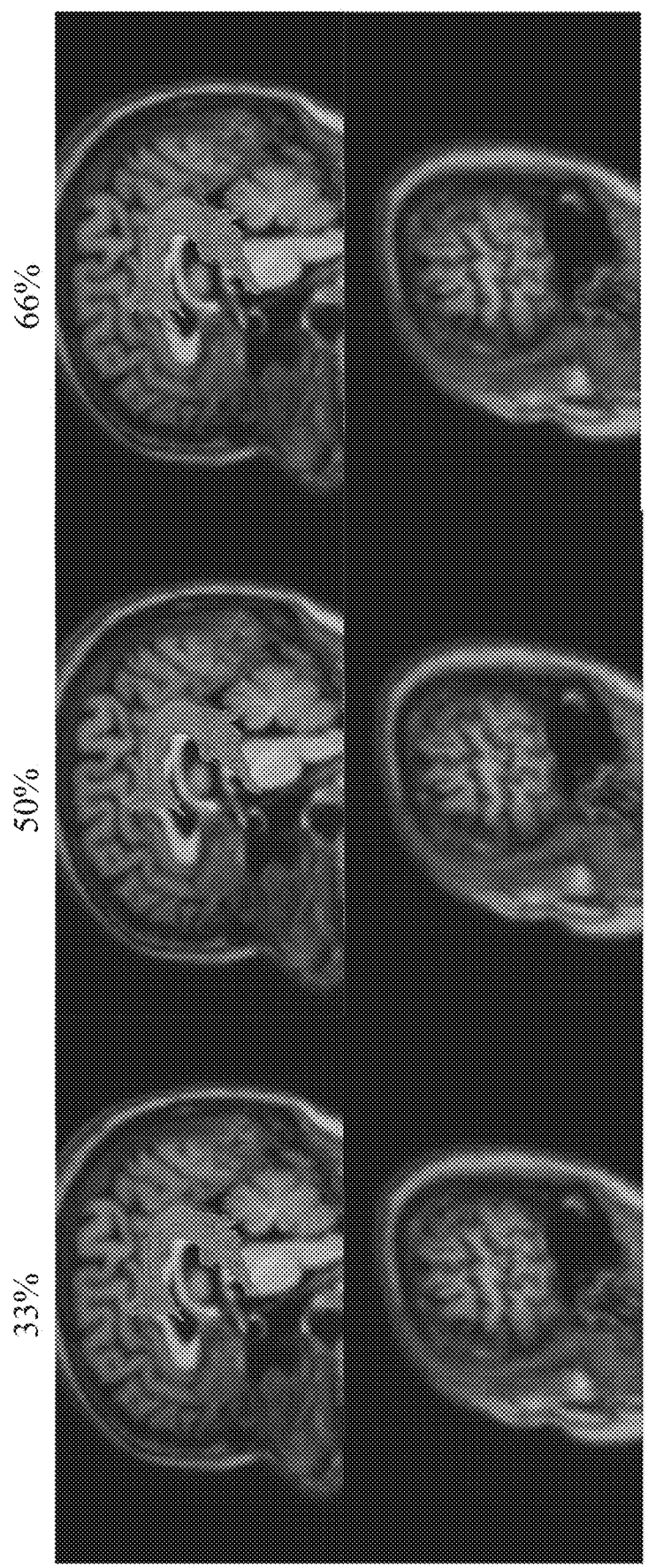
[FIG. 16]

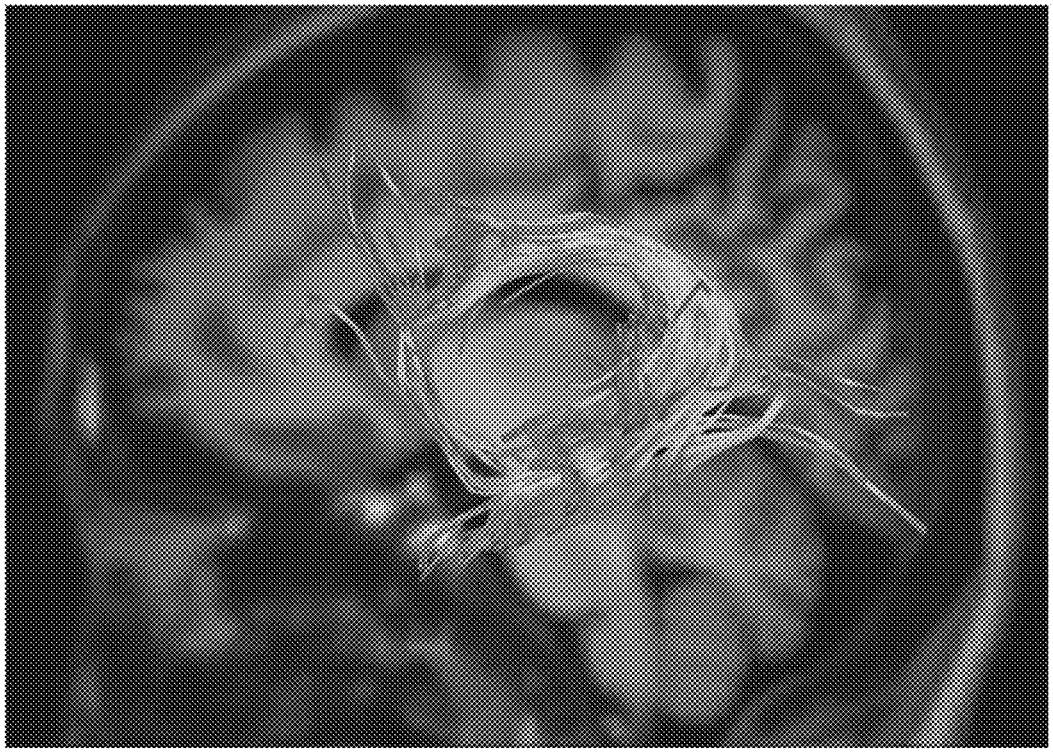
[FIG. 17]

METHOD AND APPARATUS OF FIBER TRACKING, AND NON-TRANSITORY COMPUTER-READABLE MEDIUM THEREOF

BACKGROUND

1. Technical Field

The present disclosure relates to a method and an apparatus of fiber tracking, and non-transitory computer-readable medium thereof, more particularly to a method of fiber tracking with improved sensitivity, and an apparatus using the same, and non-transitory computer-readable medium thereof.

2. Description of the Related Art

The white matter is one of three major elements of a central nervous system and formed by nerve fibers and able to communicate and transmit nerve impulses. The growth and development degree of the white matter may affect functions of learning, self-control and may cause mental disease. Therefore, the technique of the fiber reconstruction has been drawn high attention by information and neuroscience researchers.

The diffusion magnetic resonance imaging is the modern modality of choice to scrutinize the architecture of human tissue and neuronal bundles by in-vivo depicting the directional anisotropy of water molecular diffusivity. One of the most promising model is diffusion tenor imaging (DTI). Water molecular diffusion is described as an ellipsoid tensor model, and thus could be decomposed into three mutually orthogonal eigenvectors and eigenvalues: the diffusion coefficient along the direction of maximal apparent diffusion (axial diffusivity or $\lambda 1$), and the diffusion coefficients along two following orthogonal directions embedded perpendicular to the maximal diffusion direction ($\lambda 2$ and $\lambda 3$). Whole brain fiber tracking can be reconstructed according to the fractional anisotropy (FA, the standard deviation of the three eigenvalues) thresholds and the turning angles (the angle between two adjacent primary eigenvector) based on the user's previous experiences.

There are very large differences between each of the nerve fasciculus due to the cranial nerves are highly differentiated. However, the conventional fiber tracking still uses single tracking parameter (a FA threshold and a turning angle), which is selected upon experimenter's experience. As a result, there is a problem that no standard tracking parameter range is referred to establish reliable nerve fiber connections. Furthermore, the manner of using the single tracking parameter for the fiber tracking process has relatively high specificity but may underestimate or overestimate the reconstruction of the specific fasciculus. For example, for a neurosurgical patient with brain tumor, the patient's nerve fasciculus may be oppressed, pushed or even infiltrated because of the tumor growth; in this case, compared with healthy subject, the fiber tracking process for the patient with brain tumors may need to set another different turning angles and FA thresholds in order to completely track the same nerve fasciculus. Furthermore, the currently-available fiber tracking algorithms are free to adjust the tracking parameters, but fail to integrate the tracking parameters for the fiber tracking reconstruction.

According to above content, what is needed is to develop a fiber tracking method to solve the problem that no standard range of tracking parameters is built, and the problem that the direction of the nerve fasciculus may be underestimated or overestimate because of only single tracking parameter used for tracking the nerve, and the problem that the tracking parameters are not integrated for nerve tracking process.

SUMMARY

In order to solve above-mentioned problem, the present disclosure is to provide a method and an apparatus of tracking nerve, and non-transitory computer-readable medium thereof.

According to an embodiment, the present disclosure provides a method of fiber tracking, and the method includes steps of receiving a first diffusion weighted image of a subject's brain; obtaining N tracking parameters from a first relation matrix stored in a storage unit according to first N of all similarities of the first relation matrix, wherein N is a positive integer greater than or equal to 8; performing a fiber tracking process on the first diffusion weighted image according to each of the N tracking parameters, to obtain a plurality of first tracking images; obtaining two first regions of interest according to a predetermined fasciculus; extracting a plurality of nerve fibers between the two first regions of interest in each of the plurality of first tracking images; according to the plurality of nerve fibers extracted from the plurality of first tracking images, obtaining nerve fasciculus probabilities of overlapped voxels based on an overlapping equation, wherein the overlapping equation is $T_j = \text{norm}(\Sigma_{i=1}^{n} w_i \times (t_j)_i)$, and $T_j$ is a nerve fasciculus probability of the j-th overlapped voxel, $w_i$ is a similarity corresponding to the i-th predetermined tracking parameter, $(t_j)_i$ is a quantity of the nerve fibers of the j-th image voxel of the first tracking image obtained according to the i-th predetermined tracking parameter, and the j-th overlapped voxel corresponds in position to the j-th image voxel of each of the plurality of first tracking images, and i and j are positive integers; among the overlapped voxels, selecting the overlapped voxels having the top one to ten percent of nerve fasciculus probabilities to establish a nerve fasciculus skeleton; and comparing structural similarities between the nerve fasciculus skeleton and the extracted nerve fibers in each of the plurality of first tracking images, to obtain a plurality of evaluation values, and then obtaining a specific fasciculus according to the nerve fibers that having the top thirty-three to sixty-six percent of the evaluation values.

According to an embodiment, the present disclosure provides a non-transitory computer-readable medium for fiber tracking, configured to store operating instructions which are executed by at least one processor to execute operations of receiving a first diffusion weighted image of a subject's brain; obtaining N tracking parameters from a first relation matrix stored in a storage unit according to first N of all similarities of the first relation matrix, wherein N is a positive integer greater than or equal to 8; performing a fiber tracking process on the first diffusion weighted image according to each of the N tracking parameters, to obtain a plurality of first tracking images; obtaining two first regions of interest according to a predetermined fasciculus; extracting a plurality of nerve fibers between the two first regions of interest in each of the plurality of first tracking images; according to the plurality of nerve fibers extracted from the plurality of first tracking images, obtaining nerve fasciculus probabilities of overlapped voxels based on an overlapping equation, wherein the overlapping equation is $T_j = \text{norm}(\Sigma_{i=1}^{n} w_i \times (t_j)_i)$, and $T_j$ is a nerve fasciculus probability of the j-th overlapped voxel, $w_i$ is a similarity corresponding to the i-th predetermined tracking parameter, $(t_j)_i$ is a quantity of the nerve fibers of the j-th image voxel of the first tracking image obtained according to the i-th predetermined tracking parameter, and the j-th overlapped voxel corresponds in position to the j-th image voxel of each of the plurality of first tracking images, and i and j are positive integers; among the overlapped voxels, selecting the overlapped voxels having the top one to ten percent of nerve fasciculus probabilities to establish a nerve fasciculus skeleton; and comparing structural similarities between the nerve fasciculus skeleton and the extracted nerve fibers in each of the plurality of first tracking images, to obtain a plurality of evaluation values, and then obtaining a specific fasciculus according to the nerve fibers that having the top thirty-three to sixty-six percent of the evaluation values.

According to an embodiment, the present disclosure provides an apparatus of fiber tracking, and the apparatus includes at least one processor, a storage unit, and at least one program. The at least one program is stored in the storage unit and configured to be executed by the at least one processor, and at least one program comprises instructions for operations of receiving a first diffusion weighted image of a subject's brain; obtaining N tracking parameters from a first relation matrix stored in a storage unit according to first N of all similarities of the first relation matrix, wherein N is a positive integer greater than or equal to 8; performing a fiber tracking process on the first diffusion weighted image according to each of the N tracking parameters, to obtain a plurality of first tracking images; obtaining two first regions of interest according to a predetermined fasciculus; extracting a plurality of nerve fibers between the two first regions of interest in each of the plurality of first tracking images; according to the plurality of nerve fibers extracted from the plurality of first tracking images, obtaining nerve fasciculus probabilities of overlapped voxels based on an overlapping equation, wherein the overlapping equation is $T_j$=norm $(\Sigma_{i=1}^{n} w_i \times (t_j)_i)$, and $T_j$ is a nerve fasciculus probability of the j-th overlapped voxel, $w_i$ is a similarity corresponding to the i-th predetermined tracking parameter, $(t_j)_i$ is a quantity of the nerve fibers of the j-th image voxel of the first tracking image obtained according to the i-th predetermined tracking parameter, and the j-th overlapped voxel corresponds in position to the j-th image voxel of each of the plurality of first tracking images, and i and j are positive integers; among the overlapped voxels, selecting the overlapped voxels having the top one to ten percent of nerve fasciculus probabilities to establish a nerve fasciculus skeleton; and comparing structural similarities between the nerve fasciculus skeleton and the extracted nerve fibers in each of the plurality of first tracking images, to obtain a plurality of evaluation values, and then obtaining a specific fasciculus according to the nerve fibers that having the top thirty-three to sixty-six percent of the evaluation values.

According to above content, the difference between conventional technique and the technique of the present disclosure is that the technique of the present disclosure can obtain better and validated tracking parameters for fiber tracking process on the diffusion weighted image of the subject's brain, so as to obtain the first tracking images, and then extract the plurality of nerve fibers between the two first regions of interest in each of the first tracking images, and then perform the overlapping process on the nerve fibers extracted from the first tracking images, to establish the nerve fasciculus skeleton, and the nerve fibers more similar to the structure of the nerve fasciculus skeleton are selected to obtain the specific fasciculus of the subject.

By above technical means, the sensitivity of the fiber tracking process can be improved, so that the effects of preoperative assessment and surgical navigation can be improved.

BRIEF DESCRIPTION OF THE DRAWINGS

The structure, operating principle and effects of the present disclosure will be described in detail by way of various embodiments which are illustrated in the accompanying drawings.

FIG. 1 is a flowchart showing the steps in an operation of a method of fiber tracking, in accordance with the present disclosure.

FIG. 2 is a flowchart showing the steps in an operation of an embodiment of the step 20 of FIG. 1.

FIG. 3 is a flowchart showing the steps in an operation of an embodiment of the image process of the step 206 of FIG. 2.

FIG. 4 is a flowchart showing the steps in an operation of an embodiment of the similarity comparison process of the step 360 of FIG. 3.

FIG. 5 is a block diagram of an embodiment of a non-transitory computer-readable medium for fiber tracking of the present disclosure.

FIG. 6 is a block diagram of an apparatus of fiber tracking, in accordance with the present disclosure.

FIG. 7 is a schematic view of an embodiment of the steps 201 to 205.

FIG. 8 is a schematic view of an embodiment of the steps 310 to 340 included in the step 206.

FIG. 9 is a schematic view of an embodiment of the step 350.

FIG. 10 is a schematic view of an embodiment of the steps 410 to 430 included in the step 360.

FIG. 11A is a schematic view of an embodiment of a second relation matrix corresponding to SLF III anterior part.

FIG. 11B is a schematic view of an embodiment of a second relation matrix corresponding to SLF III posterior part.

FIG. 11C is a schematic view of an embodiment of a second relation matrix corresponding to AF.

FIG. 11D is a schematic view of an embodiment of a second relation matrix corresponding to IFOF.

FIG. 12 is a schematic view of an embodiment of a first relation matrix.

FIG. 13 is a first diffusion weighted image obtained in step 110.

FIG. 14 is a schematic view of an embodiment of the present disclosure, after the steps 130 to 150 are executed.

FIG. 15 is a schematic view of an embodiment of the present disclosure, after the step 170 is executed.

FIG. 16 is a schematic view of an embodiment of the preset disclosure, after the step 180 is executed.

FIG. 17 is a schematic view of AF obtained in the nerve tracking process using single tracking parameter.

DETAILED DESCRIPTION

The following embodiments of the present disclosure are herein described in detail with reference to the accompanying drawings. These drawings show specific examples of the embodiments of the present disclosure. It is to be understood that these embodiments are exemplary implementations and are not to be construed as limiting the scope of the present disclosure in any way. Further modifications to the disclosed embodiments, as well as other embodiments, are also included within the scope of the appended claims. These embodiments are provided so that this disclosure is thorough and complete, and fully conveys the inventive concept to those skilled in the art. Regarding the drawings, the relative proportions and ratios of elements in the drawings may be exaggerated or diminished in size for the sake of clarity and convenience. Such arbitrary proportions are only illustrative and not limiting in any way. The same reference numbers are used in the drawings and description to refer to the same or like parts.

It is to be understood that, although the terms 'first', 'second', 'third', and so on, may be used herein to describe various elements, these elements should not be limited by these terms. These terms are used only for the purpose of distinguishing one component from another component. Thus, a first element discussed herein could be termed a second element without altering the description of the present disclosure. As used herein, the term "or" includes any and all combinations of one or more of the associated listed items.

Before the description of the method and apparatus of fiber tracking, and non-transitory computer-readable medium of the present disclosure, the definition of the terms used in the present disclosure are explained. The tracking parameter of the present disclosure means a combination of a FA threshold and a turning angle, that is, different tracking parameter can be a combination of different FA threshold and different turning angle. The specific fasciculus described in the present disclosure means the nerve fasciculus obtained by the method of the present disclosure, and the predetermined fasciculus is the nerve fasciculus expected to obtain. The nerve fasciculi described in the present disclosure are included in the white matter of brain. Furthermore, the steps 120 to 180 described in the present disclosure can be called as an algorithm for multiple assigned criteria. Furthermore, all images described in the present disclosure should be three-dimensional images, but in order to avoid the drawing figures from too complicated, the schematic view of each embodiment of the present disclosure just shows the two-dimensional images.

The method and the apparatus of fiber tracking, and non-transitory computer-readable medium of the present disclosure will hereinafter be described in more detail, with reference to the accompanying drawings. FIG. 1 is a flowchart showing the steps in an operation of a method of fiber tracking, in accordance with the present disclosure, and the method includes steps 110 to 180. In the step 110, a first diffusion weighted image of a subject's brain is received, and in the step 120, N tracking parameters from a first relation matrix stored in a storage unit according to first N of all similarities of the first relation matrix are obtained, and N is a positive integer greater than or equal to 8. In the step 130, the fiber tracking process is performed on the first diffusion weighted image according to each of the N the tracking parameters, so as to obtain the plurality of first tracking images. In the step 140, two first regions of interest are obtained according to a predetermined fasciculus. In the step 150, nerve fibers between the two first regions of interest are extracted in each of the first tracking image. In the step 160, according to the nerve fibers extracted from the first tracking images, nerve fasciculus probabilities of a plurality of overlapped voxels can be obtained based on an overlapping equation, and the overlapping equation is: $T_j = \text{norm}(\Sigma_{i=1}^{n} w_i \times (t_j)_i)$, wherein $T^j$ is a nerve fasciculus probability of the j-th the overlapped voxel, $w_i$ is a similarity corresponding to the i-th predetermined tracking parameter, $(t_j)_i$ is a quantity of the nerve fibers existing in the j-th image voxel of the first tracking image obtained according to the i-th predetermined tracking parameter, and the j-th overlapped voxel corresponds in position to the j-th image voxel of each of the plurality of first tracking image, and i and j are positive integers. Next, in the step 170, the overlapped voxel having the top one to ten percent of values of the nerve fasciculus probabilities are selected to establish a nerve fasciculus skeleton. In the step 180, the structural similarities between the nerve fasciculus skeleton and each of the extracted nerve fibers in each first tracking image are compared to obtain a plurality of evaluation values, so as to obtain a specific fasciculus according to the plurality of nerve fibers having the top thirty-three to sixty-six percent of the evaluation values.

In the step 110, the subject can be a patient who wishes to undergo neurosurgery, but the present disclosure is not limited thereto. Through aforementioned steps 110 to 180, the patient's specific fasciculus for surgery can be obtained, and it is useful to improve effects of preoperative assessment and surgical navigation.

The first relation matrix of the step 120 is configured to express relations between the tracking parameters for tracking various nerve fasciculi and the similarities corresponding thereto. The similarities are obtained from and validated by the experiment of the T1 weighted images and diffusion weighted images of the human brain specimens and the healthy subjects. The tracking parameter having higher similarity is more useful for tracking various nerve fasciculi. In other words, the first relation matrix expresses the appropriate degrees of the tracking parameters for tracking various nerve fasciculi, and the appropriate degrees are validated by experiments; that is, the appropriate degree is higher, the similarity is higher. The experiment validating process may include the steps 201 to 207, the steps 20 to 22, the steps 310 to 360, and the steps 410 to 430, and the detail process of establishing the first relation matrix will be described in following paragraphs. Furthermore, the final target of the fiber tracking process is to obtain the nerve fasciculus which is accurate and can be extended to end of cortex, so when N is greater, more combinational tracking parameters can be used to describe various nerve fasciculi, and more complete nerve tracking process can be obtained;

furthermore, the fake nerve fasciculus caused by noise can be removed significantly, so that the reconstruction of specific nerve can be clearly shown, and the shown nerve fasciculus can be effectively extended to the end of cortex. However, larger N may cause the time for performing the method of fiber tracking of the present disclosure to be longer, so N in the step 120 can be a positive integer greater than or equal to 8, and it is enough to achieve above effect. In practice, the user operating the apparatus of fiber tracking of the present disclosure can determine and adjust the value of N upon practical demand.

In the step 130, the fiber tracking process can comprise an operation of performing the diffusion tensor analysis on the first diffusion weighted image to generate the first diffusion tensor imaging corresponding thereto, and then using the tracking parameters obtained in the step 120 to perform the fiber tracking for whole brain on the first diffusion tensor imaging, so as to obtain the first tracking images. Each first tracking image includes a plurality of image voxels.

In the step 140, the two first regions of interest can be a start region and an end region of the predetermined fasciculus in the anatomical automatic labeling (AAL) template. The predetermined fasciculus is the nerve fasciculus to be obtained after the method of the present disclosure is performed, that is, the predetermined fasciculus is also the subject's specific fasciculus which the user operating the apparatus of fiber tracking wants to construct.

A number of the nerve fiber extracted in the step 150 can be, but not limited to, at least one thousand, and when the number of the extracted nerve fiber becomes greater, the nerve tracking process can reach a stable state, but the time of executing the step 150 becomes longer. Generally, when the number of the nerve fiber is up to eight hundred, the stable state of the process can be reached, so, in consideration of time, the number of the extracted nerve fiber in the step 150 can be set to be in a range of eight hundred to two thousand. The user can adjust upon the practical demand in stable result and remodeling speed.

The nerve fasciculus probability $T_j$ of the overlapped voxel calculated in the step 160 means the probability that the nerve fiber exists in the overlapped voxel. When $T_j$ is greater, it means that the nerve fiber exists in the overlapped voxel more possibly, so that, the nerve fasciculus skeleton can be established after the step 170 of selecting the overlapped voxels having the top one to ten percent of the nerve fasciculus probabilities. It should be noted that the nerve fasciculus skeleton cannot be completely shown merely according to the overlapped voxels having the probability greater than the top one percent of the probabilities; and, the overlapped voxels having the probability lower than the top ten percent of the nerve fasciculus probabilities may have error information due to noise.

The comparison process for the structural similarities in the step 180 is to compare the overlap rates of the spatial positions. When the overlap rate of the spatial position is greater, the evaluation value is greater. In consideration of the direction of the nerve fiber bundle and the effective extension of the nerve fiber bundle to end of cortex, in the step 180 the nerve fibers having the top thirty-three to sixty-six percent of the evaluation values may be selected to establish the specific fasciculus, thereby preventing the established specific fasciculus from poorly expressing the nerve fiber extended to the end of cortex, and from having other noise to cause error message.

Through aforementioned step, the method of the present disclosure is able to obtain the better and validated tracking parameters, which are the N tracking parameters of the first relation matrix, and then extract the plurality of nerve fibers between the two first regions of interest in each of the first tracking image according to the tracking parameters, and then perform the overlapping process to establish the nerve fasciculus skeleton according to the nerve fiber extracted from the first tracking images in the steps 160 and 170, and finally select the nerve fibers more similar to the structure of the nerve fasciculus skeleton to obtain the specific fasciculus of the subject. As a result, the sensitivity of the fiber tracking process and the effects of preoperative assessment and surgical navigation can be improved.

Furthermore, before the step 120, the method of the present disclosure can include the steps 20 and 22. In the step 20, a second relation matrixes corresponding to each nerve fasciculus is obtained; and in the step 22, a mean matrix of the second relation matrixes corresponding to the plurality of nerve fasciculus is calculated to obtain the first relation matrix. The second relation matrix of the step 20 can express the relations between the tracking parameters for tracking each nerve fasciculus and the similarities corresponding thereto, and the tracking parameter having higher similarity is more useful for tracking the nerve fasciculus. In the step 22, according to the similarities corresponding to the tracking parameters, the second relation matrixes corresponding to the nerve fasciculi are summed up to calculate a mean matrix which can be served as the first relation matrix of the step 120. Through aforementioned steps 20 to 22, the method of fiber tracking of the present disclosure can comprehensively consider the appropriate ranges of the tracking parameters for each nerve fasciculus, so as to obtain the appropriate ranges of tracking parameters for tracking all nerve fasciculi.

Please refer to FIG. 2, which is a flowchart showing the steps in an operation of an embodiment of the step 20 of FIG. 1. In an embodiment: the step 20 can include steps 201 through 207 for obtaining the second relation matrix corresponding to the nerve fasciculus. Preferably, the steps 201 through 207 can be executed for several times. In the step 201, the computed tomography image of the brain specimen is obtained and the computed tomography image is labeled with a predetermined fasciculus; in the step 202, the computed tomography image is registered to a first T1 weighted image by using landmark registration, to obtain a first transformation parameter; in the step 203, the first T1 weighted image is registered to a T1 template in the MNI standard space, to obtain a second transformation parameter; in the step 204, the predetermined fasciculus labeled in the computed tomography image is extracted, and the predetermined fasciculus is registered to the MNI standard space according to the first and the second transformation parameters; in the step 205, two second regions of interest corresponding to the predetermined fasciculus in the MNI standard space are obtained according to the predetermined fasciculus labeled in the MNI standard space and an AAL template in the MNI standard space; in the step 206, the T1 weighted images and the second diffusion weighted images of each of the plurality of healthy subjects' brains are obtained, and the image process is performed on the second T1 weighted image and the second diffusion weighted image of each of the plurality of healthy subject' brains, so as to obtain the third relation matrix corresponding to the predetermined fasciculus of each of the plurality of healthy subjects; in the step 207, a mean matrix of the third relation matrixes corresponding to all the healthy subjects' brains is calculated, and the calculated mean matrix is served as the second relation matrix corresponding to the predetermined fasciculus. Through the above steps, the second relation matrix corresponding to a predetermined fasciculus can be obtained. Preferably, the steps 201 through 207 of the step 20 must be executed for multiple times, thereby obtaining the second relation matrixes corresponding to the plurality of nerve fasciculi in the white matter of brain.

The third relation matrix of the step 206 can express the relations between the tracking parameters for tracking the predetermined fasciculus of each healthy subject and the similarities corresponding thereto. In the step 207, according to the similarities corresponding to the tracking parameters, the third relation matrixes corresponding to all the healthy subjects' brains are summed up to calculate a mean matrix of the third relation matrixes, and the mean matrix can be served as the second relation matrix of the step 20. In other words, through the step 207, the method of fiber tracking of the present disclosure can comprehensively consider the appropriate ranges of the tracking parameters for predetermined fasciculus of all the healthy subjects' brains, so as to obtain the appropriate ranges of the tracking parameters for all subjects' predetermined fasciculus.

Please refer to FIG. 3, which is a flowchart showing the steps in an operation of an embodiment of the image process of the step 206 of FIG. 2. The image process of the step 206 may include steps 310 to 360. In the step 310, the second T1 weighted image is registered to a second diffusion weighted image to obtain a registration transformation parameter, and an inverse transformation is then performed on the registration transformation parameter to obtain an inverse registration transformation parameter; in the step 320, the first T1 weighted image is registered to the T1 template in the MNI standard space to obtain a third transformation parameter, and another inverse transformation is performed on the third transformation parameter to obtain a third inverse transformation parameter; in the step 330, the diffusion tensor analysis is performed on the second diffusion weighted image to reconstruct the second diffusion tensor imaging; in the step 340, the two second regions of interest corresponding to the predetermined fasciculus in the MNI standard space is transformed to the second diffusion weighted image by the third inverse transformation parameter and the registration transformation parameter, and the fiber tracking process is performed on the second diffusion tensor imaging according to the two second regions of interest transformed to the second diffusion weighted image and all of the FA thresholds and the turning angles built in the storage unit, to obtain a plurality of second tracking images; in the step 350, a mapping process with different probabilities is performed on each of the plurality of second tracking images, and each of the plurality of second tracking images can be transformed to the MNI standard space according to the third transformation parameter and the inverse registration transformation parameter; in the step 360, a similarity comparison process is performed on the predetermined fasciculus registered to the MNI standard space and the plurality of second tracking images transformed to the MNI standard space by the mapping process with different probabilities, so as to obtain the third relation matrix.

Please refer to FIG. 4, which is a flowchart showing the steps in an operation of an embodiment of a similarity comparison process of the step 360 of FIG. 3. The similarity comparison process of the step 360 includes steps 410 through 430. In the step 410, the overlap rates between the predetermined fasciculus registered to the MNI standard space and the plurality of second tracking images transformed to the MNI standard space by the mapping process with different probabilities are calculated to obtain an overlap relation matrix; in the step 420, the accuracy rates between the predetermined fasciculus registered to the MNI standard space and the plurality of second tracking images transformed to the MNI standard space by the mapping process with different probabilities are calculated to obtain an accuracy relation matrix; and, in the step 430, the overlap rates of the overlap relation matrix are multiplied by the accuracy rates of the accuracy relation matrix according to the tracking parameters corresponding thereto, so as to obtain the third relation matrix.

The overlap relation matrix of the step 410 can express correspondence relations between the tracking parameters and the overlap rates for each second tracking image, and the overlap rate corresponding to each tracking parameter can be obtained based on the overlap rate function:

$$\frac{A \cap B}{A \cup B},$$

wherein A is the second tracking image transformed to the MNI standard space by the mapping process with each probability, and B is the predetermined fasciculus registered to the MNI standard space. Based on this function, the overlap rates between the plurality of second tracking images transformed to the MNI standard space by mapping process with each probability and the predetermined fasciculus registered to the MNI standard space can be obtained; next, the overlap rates between the second tracking image transformed to the MNI standard space by the mapping process with different probabilities and the predetermined fasciculus registered to the MNI standard space are integrated, and a mean matrix of the integration result is then calculated to serve as the overlap relation matrix.

The accuracy relation matrix of the step 420 can express the corresponding relation between the tracking parameters and the accuracy rates for each second tracking image. The accuracy rate corresponding to each tracking parameter can be obtained based on the accuracy rate function:

$$\frac{C \cap D}{D},$$

wherein C is the second tracking image transformed to the MNI standard space by the mapping process with each probability, and D is the predetermined fasciculus registered to the MNI standard space. Based on this function, the accuracy rates between the plurality of second tracking images transformed to the MNI standard space by the mapping process with each probability and the predetermined fasciculus registered to the MNI standard space can be obtained; next, the accuracy rates between the plurality of second tracking images transformed to the MNI standard space by the mapping process with different probabilities and the predetermined fasciculus registered to the MNI standard space are integrated, and a mean matrix of the integration result is calculated to obtain.

Please refer to FIG. 5, which is a block diagram of an embodiment of non-transitory computer-readable medium for fiber tracking of the present disclosure. The non-transitory computer-readable medium 500 for fiber tracking can include operating instructions 502 which can be executed by at least one processor 504 to perform above-mentioned method of fiber tracking. The operating instructions may include any other step in the description herein. The operating instructions 502 can be stored in the non-transitory computer-readable medium 500. For example, the non-transitory computer-readable medium 500 can be storage medium such as a disk, an optical disk or a magnetic tape, or any non-transitory computer-readable medium known in the art.

Please refer to FIG. 6, which is a block diagram of the apparatus of fiber tracking of the present disclosure. The apparatus 600 includes a processor 602, a storage unit 604 and a program 606. The program 606 is stored in the storage unit and can be executed by at least one processor 602; for example, the program 606 may include the above-mentioned operating instructions for the method of tracking nerve of the present disclosure. A number of each of the processor 602, the storage unit 604 and the program 606 can be one, but the present disclosure is not limited thereto, and can be adjusted upon practical demand.

The following describe an embodiment in cooperation with FIGS. 7 through 17.

Establishment of the First Relation Matrix

The first relation matrix is obtained by calculating a mean matrix of the second relation matrixes corresponding to the nerve fasciculi according to the similarities corresponding to the tracking parameters. In this embodiment, the steps 201 through 207 are described based on the operations of obtaining the second relation matrix corresponding to arcuate fasciculus (AF), so as to obtain the first relation matrix of the present disclosure. For example, the second relation matrixes corresponding to four nerve fasciculi of the white matter of brain including superior longitudinal fasciculus III anterior part (SLFIII anterior part), superior longitudinal fasciculus III posterior part (SLF III posterior part), AF and inferior fronto-occipital fasciculus (IFOF) can be summed up according to the similarities corresponding to the tracking parameters, and the mean matrix of the second relation matrixes can be served as the first relation matrix of this embodiment.

Please refer to FIG. 7, which is a schematic view of an embodiment of the steps 201 to 205. In this embodiment, the predetermined fasciculus can be AF. A half post-mortem human brain specimen, which has been fixed in formalin for 2 years, is taken as example of the brain specimen in this embodiment. In the steps 202 and 203, two white points at left and right sides of the first T1 weighted image and the computed tomography image are landmarks. The computed tomography image is registered to the first T1 weighted image, so as to obtain a first transformation parameter, and the first T1 weighted image is then registered to the MNI standard space, to obtain a second transformation parameter. In the step 204, the AF labeled on the computed tomography image is transformed to the MNI standard space. In the step 205, through the AF image transformed and overlapped to the MNI standard space according to the AAL template in the MNI standard space, ROIs corresponding to AF can be found, such as ROI1 and ROI2 of figures, and they are second regions of interest. It should be noted that, the structure of the nerve fasciculus of white matter of brain is a three-dimensional structure, and in order to describe the features of the embodiment easily, the images of the steps are shown by two-dimensional images with different angles. The 3D structure corresponding to the 2D images is well-known for one skilled in the art, so the detailed description is not repeated.

Please refer to FIGS. 8, 9 and 10. FIG. 8 is a schematic view of an embodiment of the steps 310 to 340 included in the step 206, FIG. 9 is a schematic view of an embodiment of the step 350, and FIG. 10 is a schematic view of an embodiment of the steps 410 to 430 included in the step 360. In this embodiment, a number of healthy subjects is 10, and the ten healthy subjects include 6 women and 4 men, and their average age is about 57 years old. The steps of obtaining the third relation matrix corresponding to each healthy subject's AF are the same, for example, the third relation matrix corresponding to each healthy subject's AF is obtained through the steps 310 and 360. FIGS. 8 through 10 show an example of the third relation matrix corresponding to AF obtained by performing the image process on the second T1 weighted image and the second diffusion weighted image of one healthy subject's brain, and the third relation matrixes corresponding to the other 9 healthy subjects' AF can be obtained by similar manner.

The 3T MRI scanner, manufactured by Siemens Trio, is used to scan and obtain the second T1 weighted image and the second diffusion weighted image of the healthy subject's brain. The parameters for scanning the second T1 weighted image are TR/TE=2500/27 ms, matrix=256×256, FOV=192×192 mm, voxel size=1×1×1 mm$^3$; and, the parameters for scanning the second diffusion weighted image (DWI) are TR/TE=11000/104 ms, voxel size=2×2×2 mm$^3$, b-value=1000 s/mm$^2$, diffusion encoding direction=30, and NEX=3.

The FA thresholds built in the storage unit is in a range of 0.10 to 0.30, the turning angles are in a range of 20° to 80°. Each tracking parameter is a combination of one of the FA thresholds in the preset range, and one of the turning angles in the preset range; in other words, in this embodiment, a number of the tracking parameters built in the storage unit is 35, and each tracking parameter can be used to generate a second tracking image. A mapping process with different probabilities is performed on each of the plurality of second tracking images, and after transformed to the MNI standard space, the similarity comparison process is performed the transformed second tracking image with AF registered to the MNI standard space to obtain the overlap rate and the accuracy rate (the steps 410 and 420). Next, a product of the overlap rates and the accuracy rates of each tracking parameter can be served as the third relation matrix (step 430). As a result, after the third relation matrixes corresponding to the ten healthy subject's AFs are obtained, the mean matrix of the third relation matrixes can be served as the second relation matrix corresponding to the AF (the step 207).

In this embodiment, FIG. 11A shows the second relation matrix corresponding to SLF III anterior part; the second relation matrix corresponding to SLF III posterior part is shown in FIG. 11B; the second relation matrix corresponding to AF is shown in FIG. 11C, and the second relation matrix corresponding to IFOF is shown in FIG. 11D. FIG. 12 is a schematic view of an embodiment of a first relation matrix, the second relation matrixes can be summed up according to the tracking parameters to obtain the mean matrix of the second relation matrixes, and the mean matrix can be served as the first relation matrix (the step 22).

The Construction of the Subject's Specific Fasciculus

Please refer to FIG. 13, which is a first diffusion weighted image obtained in step 110. Please also refer to FIG. 12. The horizontal axe represents the turning angle and the vertical axe represents the FA threshold, and a tracking parameter can be formed by a turning angle and a FA threshold. In this embodiment, different magnitude of the similarity corresponding to each tracking parameter is represented by color with different brightness level, that is, the deeper color means lower similarity and the lighter color means higher similarity; however, the present disclosure is not limited to this embodiment, for example, the magnitude of similarity corresponding to each tracking parameter can be directly represented by data. In this embodiment, the experimenter selects eight tracking parameters more appropriate to requirement thereof, for example, the eight tracking parameters (such as the blocks with black flames in FIG. 12) may include: FA threshold=0.20 and turning angle=60°, that is, similarity=0.5255; FA threshold=0.25 and turning angle=70°, that is, similarity=0.5195; FA threshold=0.25 and turning angle=80°, that is, similarity=0.5189; FA threshold=0.25 and turning angle=60°, that is, similarity=0.5170; FA threshold=0.20 and turning angle=50°, that is, similarity=0.5162; FA threshold=0.25 and turning angle=50°, that is, similarity=0.5080; FA threshold=0.20 and turning angle=70°, that is, similarity=0.5070; FA threshold=0.30 and turning angle=70°, that is, similarity=0.4984. Next, the fiber tracking process is performed according to the eight tracking parameters (the step 120).

Please refer to FIG. 14, which is a schematic view of an embodiment of the present disclosure, after the steps 130 to 150 are executed. The fiber tracking process can be performed based on each tracking parameter to generate a first tracking image; in this case, the process is for fiber tracking of whole brain. Next, according to the first region of interest corresponding to the predetermined fasciculus of this embodiment, the plurality of nerve fibers between the two first regions of interest are extracted; for example, the nerve fibers predetermined to construct the predetermined fasciculus are extracted. In this embodiment, the specific fasciculus can be AF, so the two first regions of interest are equal to the two second regions of interest. FIG. 14 shows eight more appropriate tracking parameters for nerve tracking process, and shows a result of extracting the plurality of nerve fibers between the two first regions of interest. In order to avoid the drawing figures from too complicated, only the extracted nerve fibers between the two first regions of interest in each first tracking image are drawn, and the structure and position of whole brain are not shown in the figures. In this embodiment, the number of the nerve fibers between the two first regions of interest can be one thousand.

Please refer to FIG. 15, which is a schematic view of an embodiment of the present disclosure, after the step 170 is executed. In this embodiment, the overlapped voxels with the top one percent, top five percent, or top ten percent of nerve fasciculus probabilities, can be selected to establish the nerve fasciculus skeleton. The following describes the step 180 according to the nerve fasciculus skeleton established by the overlapped voxels with top ten percent of nerve fasciculus probabilities.

Please refer to FIG. 16, which is a schematic view of an embodiment of the preset disclosure, after the step 180 is executed. In this embodiment, the nerve fibers with top thirty-three, top fifty percent, or top sixty-six of evaluation values can be selected to obtain the specific fasciculus. As shown in FIG. 16, when the nerve fibers with top thirty-three to sixty-six of evaluation values are selected to establish the specific fasciculus, it can prevent the established specific fasciculus from poorly expressing the nerve fiber extended to the end of cortex, and from having other noise to cause error message.

Compared with the result of using single tracking parameter including, for example, FA threshold=0.2 and turning angle=60° (as shown in FIG. 17), the method of fiber tracking of the present disclosure can more accurately reconstruct the direction of nerve fibers and the end of cortex of the arcuate fasciculus, as shown in FIG. 16. As a result, the effects of the preoperative assessment and navigation in neurosurgical surgery can be improved.

To summarize, the difference between the conventional technique and the technique of the present disclosure is that the technique of the present disclosure uses the better and validated tracking parameters to perform the fiber tracking process on the diffusion weighted image of the subject's brain, so as to obtain the first tracking images, and extracts the plurality of nerve fibers between the two first regions of interest in each of the plurality of first tracking images, and then perform the overlapping process on the nerve fiber extracted from the first tracking images to establish the nerve fasciculus skeleton, and finally, the nerve fibers more similar to the structure of the nerve fasciculus skeleton are selected to obtain the specific fasciculus of the subject, thereby improving sensitivity of the nerve tracking process, and improving the effects of preoperative assessment and surgical navigation.

The present disclosure disclosed herein has been described by means of specific embodiments. However, numerous modifications, variations and enhancements can be made thereto by those skilled in the art without departing from the spirit and scope of the disclosure set forth in the claims.

What is claimed is:

1. A method of fiber tracking, comprising:
receiving a first diffusion weighted image of a subject's brain;
obtaining N tracking parameters from a first relation matrix stored in a storage unit according to first N of all similarities of the first relation matrix, wherein N is a positive integer greater than or equal to 8;
performing a fiber tracking process on the first diffusion weighted image according to each of the N tracking parameters, to obtain a plurality of first tracking images;
obtaining two first regions of interest according to a predetermined fasciculus;
extracting a plurality of nerve fibers between the two first regions of interest in each of the plurality of first tracking images;
according to the plurality of nerve fibers extracted from the plurality of first tracking images, obtaining nerve fasciculus probabilities of overlapped voxels based on an overlapping equation, wherein the overlapping equation is $T_j=\text{norm}(\Sigma_{i=1}^{n} w_i \times (t_j)_i)$, and $T_j$ is a nerve fasciculus probability of the j-th overlapped voxel, $w_i$ is a similarity corresponding to the i-th predetermined tracking parameter, $(t_j)_i$ is a quantity of the nerve fibers of the j-th image voxel of the first tracking image obtained according to the i-th predetermined tracking parameter, and the j-th overlapped voxel corresponds in position to the j-th image voxel of each of the plurality of first tracking images, and i and j are positive integers;
among the overlapped voxels, selecting the overlapped voxels having the top one to ten percent of nerve fasciculus probabilities to establish a nerve fasciculus skeleton; and
comparing structural similarities between the nerve fasciculus skeleton and the extracted nerve fibers in each of the plurality of first tracking images, to obtain a plurality of evaluation values, and then obtaining a specific fasciculus according to the nerve fibers having the top thirty-three to sixty-six percent of the evaluation values.

2. The method of fiber tracking according to claim 1, before the step of obtaining the N tracking parameters from the first relation matrix stored in the storage unit according to the first N of all similarities of the first relation matrix, the method further comprising:
obtaining a second relation matrix corresponding to each of a plurality of nerve fasciculus; and
obtaining a mean matrix of the second relation matrixes corresponding to each of the plurality of nerve fasciculus, so as to obtain the first relation matrix.

3. The method of fiber tracking according to claim 2, wherein the step of obtaining the second relation matrixes corresponding to the plurality of nerve fasciculus, comprises:
obtaining a computed tomography image of a brain specimen, wherein the computed tomography image is labeled with a predetermined fasciculus;
registering the computed tomography image to a first T1 weighted image by using landmark registration, to obtain a first transformation parameter;

registering the first T1 weighted image to a T1 template in a MNI standard space, to obtain a second transformation parameter;

extracting the predetermined fasciculus labeled in the computed tomography image, and registering the predetermined fasciculus to the MNI standard space according to the first and the second transformation parameters;

obtaining two second regions of interest corresponding to the predetermined fasciculus in the MNI standard space according to the predetermined fasciculus labeled in the MNI standard space and an anatomical automatic labeling (AAL) template in the MNI standard space;

obtaining a second T1 weighted image and a second diffusion weighted image of each of healthy subjects' brains, and performing an image process on the second T1 weighted image and the second diffusion weighted image of the healthy subjects' brains, so as to obtain a third relation matrix corresponding to the predetermined fasciculus of each of the healthy subjects' brains, wherein the image process comprises:

registering the second T1 weighted image to a second diffusion weighted image, to obtain a registration transformation parameter, and then performing an inverse transformation on the registration transformation parameter to obtain an inverse registration transformation parameter;

registering the second T1 weighted image to the T1 template in the MNI standard space, to obtain a third transformation parameter, and then performing another inverse transformation on the third transformation parameter to obtain a third inverse transformation parameter;

performing a diffusion tensor analysis on the second diffusion weighted image to reconstruct a second diffusion tensor imaging (DTI);

transforming the two second regions of interest corresponding to the predetermined fasciculus in the MNI standard space to the second diffusion weighted image by the third inverse transformation parameter and the registration transformation parameter, and then performing the fiber tracking process on the second DTI according to the two second regions of interest transformed to the second diffusion weighted image and all of fractional anisotropy (FA) thresholds and turning angles built in the storage unit, so as to obtain a plurality of second tracking images;

performing a mapping process with different probabilities on each of the plurality of second tracking images, and transforming each of the plurality of second tracking images to the MNI standard space according to the third transformation parameter and the inverse registration transformation parameter; and performing a similarity comparison process on the predetermined fasciculus registered to the MNI standard space and the plurality of second tracking images transformed to the MNI standard space by the mapping process with different probabilities, so as to obtain the third relation matrixes; and calculating a mean matrix of the third relation matrixes corresponding to the predetermined fasciculus of all the healthy subjects' brains, so as to obtain the second relation matrix corresponding to the predetermined fasciculus.

4. The method of fiber tracking according to claim 3, wherein the similarity comparison process comprises:

calculating the overlap rates between the predetermined fasciculus registered to the MNI standard space and the plurality of second tracking images transformed to the MNI standard space by the mapping process with different probabilities, so as to obtain an overlap relation matrix;

calculating accuracy rates between the predetermined fasciculus registered to the MNI standard space and the plurality of second tracking images transformed to the MNI standard space by the mapping process with different probabilities, so as to obtain an accuracy relation matrix; and multiplying the overlap rates of the overlap relation matrix by the accuracy rates of the accuracy relation matrix according to the tracking parameters corresponding thereto, so as to obtain the third relation matrix.

5. A non-transitory computer-readable medium for fiber tracking, configured to store operating instructions which are executed by at least one processor to execute following operations:

receiving a first diffusion weighted image of a subject's brain;

obtaining N tracking parameters from a first relation matrix stored in a storage unit according to first N of all similarities of the first relation matrix, wherein N is a positive integer greater than or equal to 8;

performing a fiber tracking process on the first diffusion weighted image according to each of the N tracking parameters, to obtain a plurality of first tracking images;

obtaining two first regions of interest according to a predetermined fasciculus;

extracting a plurality of nerve fibers between the two first regions of interest in each of the plurality of first tracking images;

according to the plurality of nerve fibers extracted from the plurality of first tracking images, obtaining nerve fasciculus probabilities of overlapped voxels based on an overlapping equation, wherein the overlapping equation is $T_j=\text{norm}(\Sigma_{i=1}^{n} w_i \times (t_j)_i)$, and $T_j$ is a nerve fasciculus probability of the j-th overlapped voxel, $w_i$ is a similarity corresponding to the i-th predetermined tracking parameter, $(t_j)_i$ is a quantity of the nerve fibers of the j-th image voxel of the first tracking image obtained according to the i-th predetermined tracking parameter, and the j-th overlapped voxel corresponds in position to the j-th image voxel of each of the plurality of first tracking images, and i and j are positive integers;

among the overlapped voxels, selecting the overlapped voxels having the top one to ten percent of nerve fasciculus probabilities to establish a nerve fasciculus skeleton; and comparing structural similarities between the nerve fasciculus skeleton and the extracted nerve fibers in each of the plurality of first tracking images, to obtain a plurality of evaluation values, and then obtaining a specific fasciculus according to the nerve fibers having the top thirty-three to sixty-six percent of the evaluation values.

6. The non-transitory computer-readable medium according to claim 5, wherein before the instruction of obtaining the N tracking parameters from the first relation matrix stored in the storage unit according to the first N of all similarities of the first relation matrix, the at least one processor further executes operations of:

obtaining a second relation matrix corresponding to each of a plurality of nerve fasciculus; and obtaining a mean matrix of the second relation matrixes corresponding to each of the plurality of nerve fasciculus, so as to obtain the first relation matrix.

7. The non-transitory computer-readable medium according to claim 6, wherein the operation of obtaining the second relation matrixes corresponding to the plurality of nerve fasciculus, further comprises:

obtaining a computed tomography image of a brain specimen, wherein the computed tomography image is labeled with a predetermined fasciculus;

registering the computed tomography image to a first T1 weighted image by using landmark registration, to obtain a first transformation parameter;

registering the first T1 weighted image to a T1 template in a MNI standard space, to obtain a second transformation parameter;

extracting the predetermined fasciculus labeled in the computed tomography image, and registering the predetermined fasciculus to the MNI standard space according to the first and the second transformation parameters;

obtaining two second regions of interest corresponding to the predetermined fasciculus in the MNI standard space according to the predetermined fasciculus labeled in the MNI standard space and an anatomical automatic labeling (AAL) template in the MNI standard space;

obtaining a second T1 weighted image and a second diffusion weighted image of each of healthy subjects' brains, and performing an image process on the second T1 weighted image and the second diffusion weighted image of the healthy subjects' brains, so as to obtain a third relation matrix corresponding to the predetermined fasciculus of each of the healthy subjects' brains, wherein the image process comprises:

registering the second T1 weighted image to a second diffusion weighted image, to obtain a registration transformation parameter, and then performing an inverse transformation on the registration transformation parameter to obtain an inverse registration transformation parameter;

registering the second T1 weighted image to the T1 template in the MNI standard space, to obtain a third transformation parameter, and then performing another inverse transformation on the third transformation parameter to obtain a third inverse transformation parameter;

performing a diffusion tensor analysis on the second diffusion weighted image to reconstruct a second diffusion tensor imaging (DTI);

transforming the two second regions of interest corresponding to the predetermined fasciculus in the MNI standard space to the second diffusion weighted image by the third inverse transformation parameter and the registration transformation parameter, and then performing the fiber tracking process on the second DTI according to the two second regions of interest transformed to the second diffusion weighted image and all of fractional anisotropy (FA) thresholds and turning angles built in the storage unit, so as to obtain a plurality of second tracking images;

performing a mapping process with different probabilities on each of the plurality of second tracking images, and transforming each of the plurality of second tracking images to the MNI standard space according to the third transformation parameter and the inverse registration transformation parameter; and performing a similarity comparison process on the predetermined fasciculus registered to the MNI standard space and the plurality of second tracking images transformed to the MNI standard space by the mapping process with different probabilities, so as to obtain the third relation matrixes; and calculating a mean matrix of the third relation matrixes corresponding to the predetermined fasciculus of all the healthy subjects' brains, so as to obtain the second relation matrix corresponding to the predetermined fasciculus.

8. The non-transitory computer-readable medium according to claim 7, wherein the similarity comparison process comprises:

calculating the overlap rates between the predetermined fasciculus registered to the MNI standard space and the plurality of second tracking images transformed to the MNI standard space by the mapping process with different probabilities, so as to obtain an overlap relation matrix;

calculating accuracy rates between the predetermined fasciculus registered to the MNI standard space and the plurality of second tracking images transformed to the MNI standard space by the mapping process with different probabilities, so as to obtain an accuracy relation matrix; and multiplying the overlap rates of the overlap relation matrix by the accuracy rates of the accuracy relation matrix according to the tracking parameters corresponding thereto, so as to obtain the third relation matrix.

9. An apparatus of fiber tracking, comprising:

at least one processor;

a storage unit; and at least one program stored in the storage unit and configured to be executed by the at least one processor, and at least one program comprises instructions for operations of:

receiving a first diffusion weighted image of a subject's brain;

obtaining N tracking parameters from a first relation matrix stored in a storage unit according to first N of all similarities of the first relation matrix, wherein N is a positive integer greater than or equal to 8;

performing a fiber tracking process on the first diffusion weighted image according to each of the N tracking parameters, to obtain a plurality of first tracking images;

obtaining two first regions of interest according to a predetermined fasciculus;

extracting a plurality of nerve fibers between the two first regions of interest in each of the plurality of first tracking images;

according to the plurality of nerve fibers extracted from the plurality of first tracking images, obtaining nerve fasciculus probabilities of overlapped voxels based on an overlapping equation, wherein the overlapping equation is $T_j = \mathrm{norm}(\Sigma_{i=1}^{n} w_i \times (t_j)_i)$, and $T_j$ is a nerve fasciculus probability of the j-th overlapped voxel, $w_i$ is a similarity corresponding to the i-th predetermined tracking parameter, $(t_j)_i$ is a quantity of the nerve fibers of the j-th image voxel of the first tracking image obtained according to the i-th predetermined tracking parameter, and the j-th overlapped voxel corresponds in position to the j-th image voxel of each of the plurality of first tracking images, and i and j are positive integers;

among the overlapped voxels, selecting the overlapped voxels having the top one to ten percent of nerve fasciculus probabilities to establish a nerve fasciculus skeleton; and comparing structural similarities between the nerve fasciculus skeleton and the extracted nerve fibers in each of the plurality of first tracking images, to obtain a plurality of evaluation values, and then obtaining a specific fasciculus according to the nerve fibers having the top thirty-three to sixty-six percent of the evaluation values.

* * * * *